US012462912B2

(12) United States Patent
Breton et al.

(10) Patent No.: US 12,462,912 B2
(45) Date of Patent: Nov. 4, 2025

(54) SYSTEM AND METHOD FOR PHYSICAL ACTIVITY INFORMED DRUG DOSING

(71) Applicant: The University of Virginia Licensing and Ventures Group, Charlottesville, VA (US)

(72) Inventors: Marc D. Breton, Charlottesville, VA (US); Stephen D. Patek, Charlottesville, VA (US); Basak Ozaslan, Charlottesville, VA (US)

(73) Assignee: The University of Virginia Licensing and Ventures Group, Charlottesville, VA (US)

( * ) Notice: Subject to any disclaimer, the term of this patent is extended or adjusted under 35 U.S.C. 154(b) by 45 days.

(21) Appl. No.: 16/274,874

(22) Filed: Feb. 13, 2019

(65) Prior Publication Data

US 2019/0252055 A1 Aug. 15, 2019

Related U.S. Application Data

(60) Provisional application No. 62/629,849, filed on Feb. 13, 2018.

(51) Int. Cl.
*G16H 20/10* (2018.01)
*G16H 10/40* (2018.01)
(Continued)

(52) U.S. Cl.
CPC ............. *G16H 20/10* (2018.01); *G16H 10/40* (2018.01); *G16H 10/60* (2018.01); *G16H 20/60* (2018.01); *G16H 50/30* (2018.01)

(58) Field of Classification Search
CPC ........ G16H 20/10; G16H 20/60; G16H 10/40; G16H 10/60; G16H 50/30
See application file for complete search history.

(56) References Cited

U.S. PATENT DOCUMENTS

| | | | |
|---|---|---|---|
| 3,294,770 | A | 12/1966 | Mario et al. |
| 8,135,548 | B2 | 3/2012 | Breton et al. |

(Continued)

FOREIGN PATENT DOCUMENTS

| | | | |
|---|---|---|---|
| DK | 106826 | C | 3/1967 |
| WO | 2008052199 | A2 | 5/2008 |

(Continued)

OTHER PUBLICATIONS

"Lack of Glucagon Response to Hypoglycemia in Diabetes: Evidence for an Intrinsic Pancreatic Alpha Cell Defect", Science. Available at: http://science.sciencemag.org/content/182/4108/171 (Accessed: Jun. 27, 2017).

(Continued)

*Primary Examiner* — Sheetal R Paulson
(74) *Attorney, Agent, or Firm* — Buchanan Ingersoll & Rooney PC

(57) ABSTRACT

A computer-implemented method for treating a patient suffering from Type I Diabetes (T1D). The method can include quantifying physical activity (PA) of the patient; calculating an accumulated PA periodically based on the quantified PA, the accumulated PA indicating an aggregate of the PA; and generating an activity informed insulin bolus by adjusting a prevalent functional insulin therapy bolus with a previous activity component, wherein the previous activity component is based on the accumulated daily PA, an activity profile, and an activity factor of the patient. The method can include determining an additional glucose uptake within a time period, the additional glucose uptake being caused by a PA; translating the additional glucose uptake into a number of insulin units with a same BG lowering impact; and generating an activity informed insulin bolus by adjusting a prevalent functional insulin therapy bolus with the insulin units.

25 Claims, 21 Drawing Sheets

(51) Int. Cl.

| | |
|---|---|
| ***G16H 10/60*** | (2018.01) |
| ***G16H 20/60*** | (2018.01) |
| ***G16H 50/30*** | (2018.01) |

(56) References Cited

U.S. PATENT DOCUMENTS

| | | | | |
|---|---|---|---|---|
| 8,562,587 | B2 | 10/2013 | Kovatchev et al. | |
| 8,585,593 | B2 | 11/2013 | Kovatchev et al. | |
| 8,718,958 | B2 | 5/2014 | Breton et al. | |
| 8,840,582 | B2 * | 9/2014 | Blomquist | A61M 5/14244 604/67 |
| 9,317,657 | B2 | 4/2016 | Breton et al. | |
| 9,398,869 | B2 | 7/2016 | Kovatchev et al. | |
| 9,430,022 | B2 | 8/2016 | Kovachev et al. | |
| 9,750,438 | B2 | 9/2017 | Kovatchev et al. | |
| 9,882,660 | B2 | 1/2018 | Breton et al. | |
| 2008/0172205 | A1 | 7/2008 | Breton et al. | |
| 2010/0057043 | A1 * | 3/2010 | Kovatchev | G16H 20/17 600/301 |
| 2010/0138197 | A1 * | 6/2010 | Sher | G16H 50/50 703/2 |
| 2010/0179768 | A1 | 7/2010 | Kovatchev et al. | |
| 2010/0198520 | A1 | 8/2010 | Breton et al. | |
| 2010/0249561 | A1 | 9/2010 | Patek et al. | |
| 2011/0098548 | A1 * | 4/2011 | Budiman | G16Z 99/00 600/365 |
| 2011/0264374 | A1 | 10/2011 | Johnson et al. | |
| 2011/0264378 | A1 | 10/2011 | Breton et al. | |
| 2012/0059353 | A1 | 3/2012 | Kovatchev et al. | |
| 2012/0078067 | A1 | 3/2012 | Kovatchev et al. | |
| 2012/0191361 | A1 | 7/2012 | Kovatchev et al. | |
| 2013/0079613 | A1 | 3/2013 | Kovatchev et al. | |
| 2013/0116649 | A1 | 5/2013 | Breton et al. | |
| 2014/0058749 | A1 * | 2/2014 | Galley | G16H 40/63 705/3 |
| 2014/0215239 | A1 | 7/2014 | Kovatchev et al. | |
| 2015/0018633 | A1 | 1/2015 | Kovachev et al. | |
| 2015/0190098 | A1 | 7/2015 | Patek et al. | |
| 2015/0193589 | A1 | 7/2015 | Ortiz et al. | |
| 2016/0004813 | A1 | 1/2016 | Kovatchev et al. | |
| 2016/0171183 | A1 | 6/2016 | Breton et al. | |
| 2017/0056591 | A1 | 3/2017 | Breton et al. | |
| 2017/0337348 | A1 | 11/2017 | Kovatchev et al. | |
| 2018/0020988 | A1 | 1/2018 | Patek | |
| 2018/0055452 | A1 | 3/2018 | Breton | |
| 2018/0279914 | A1 | 10/2018 | Patek et al. | |
| 2018/0313815 | A1 | 11/2018 | Kovatchev et al. | |
| 2018/0366223 | A1 | 12/2018 | Breton et al. | |
| 2020/0268968 | A1 * | 8/2020 | Steil | G16H 40/63 |

FOREIGN PATENT DOCUMENTS

| | | | |
|---|---|---|---|
| WO | 2008067284 | A2 | 6/2008 |
| WO | 2008157780 | A1 | 12/2008 |
| WO | 2008157781 | A1 | 12/2008 |
| WO | 2009026381 | A2 | 2/2009 |
| WO | 2009009528 | A3 | 3/2009 |
| WO | 2010062898 | A1 | 6/2010 |
| WO | 2010099313 | A1 | 9/2010 |
| WO | 2010138848 | A1 | 12/2010 |
| WO | 2011028925 | A1 | 3/2011 |
| WO | 2011112974 | A1 | 9/2011 |
| WO | 2011119832 | A1 | 9/2011 |
| WO | 2012178113 | A1 | 12/2012 |
| WO | 2012178134 | A2 | 12/2012 |
| WO | 2013032965 | A1 | 3/2013 |
| WO | 2014022864 | A1 | 2/2014 |
| WO | 2014130841 | A1 | 8/2014 |
| WO | 2015003124 | A2 | 1/2015 |
| WO | 2016133879 | A1 | 8/2016 |
| WO | 2016200970 | A1 | 12/2016 |
| WO | 2016201120 | A1 | 12/2016 |
| WO | 2017040927 | A1 | 3/2017 |
| WO | 2017058927 | A1 | 4/2017 |
| WO | 2017070553 | A1 | 4/2017 |
| WO | 2017132663 | A1 | 8/2017 |
| WO | 2017189957 | A1 | 11/2017 |

OTHER PUBLICATIONS

Brazeau, A.-S. et al., "Barriers to Physical Activity Among Patients With Type 1 Diabetes", Diabetes Care, vol. 31, No. 11, 108-2109 Nov. 2008.

Chimen, M. et al., "What are the health benefits of physical activity in type 1 diabetes mellitus? A literature review", Diabetologia, 55, 542-551 (2012).

Clarke, W. et al., "Statistical Tools to Analyze Continuous Glucose Monitor Data", Diabetes Technology & Therapeutics, vol. 11 Supplement 1, S-45-S-54 (2009).

Colberg, S. R. et al., "Physical Activity/Exercise and Diabetes: A Position Statement of the American Diabetes Association", Diabetes Care, vol. 39, 2065-2079, Nov. 2016.

Epstein, F.H., "Glucose Transporters and Insulin Action—Implications for Insulin Resistance and Diabetes Mellitus", The New England Journal of Medicine, Available at: http://www.nejm.org/doi/full/10.1056/nejm199907223410406. (Accessed: Jun. 27, 2017).

MacDonald, M.J., "Postexercise Late-Onset Hypoglycemia in Insulin-Dependent Diabetic Patients", Diabetes Care, vol. 10, No. 5, 584-588 Sep.-Oct. 1987.

Maran, A. et al., "Continuous Glucose Monitoring Reveals Delayed Nocturnal Hypoglycemia After Intermittent High-Intensity Exercise in Nontrained Patients with Type 1 Diabetes", Diabetes Technology & Therapeutics, vol. 12, No. 10, 763-768 (2010).

Marliss, E. B. e al., "Intense Exercise Has Unique Effects on Both Insulin 30 Release and Its Roles in Glucoregulation", Diabetes, vol. 51, S271-S283 (2002).

McMahon, S. K. et al., "Glucose Requirements to Maintain Euglycemia after Moderate-Intensity Afternoon Exercise in Adolescents with Type 1 Diabetes Are Increased in a Biphasic Manner", . J. Clin. Endocrinol. Metab. 92, 963-968 (2007).

Warburton, D. E. R., "Health benefits of physical activity: the evidence", Can. Med. Assoc. J., vol. 174, No. 6, 801-809, Mar. 14, 2006.

* cited by examiner

SYSTEM AND METHOD FOR PHYSICAL ACTIVITY INFORMED DRUG DOSING

RELATED APPLICATION

This application claims the benefit under 35 U.S.C. § 119 of U.S. Provisional Patent No. 62/629,849 filed on Feb. 13, 2018, the entire contents of which are hereby incorporated by reference in their entirety.

STATEMENT REGARDING FEDERALLY SPONSORED RESEARCH OR DEVELOPMENT

This disclosure was made with government support under Grant No. DK106826 awarded by the National Institutes of Health. The U.S. government has certain rights in the disclosure.

FIELD

An aspect of an embodiment of the present disclosure provides a system and method, for physical activity informed drug dosing.

BACKGROUND INFORMATION

Being physically active has been shown to be beneficial for both mental and physical health in the general population. Warburton et al. notes that "[t]here appears to be a linear relation between physical activity and health status, such that a further increase in physical activity and fitness will lead to additional improvements in health status.". While patients with type 1 diabetes (T1D) can also harness these benefits, PA may cause hurdles in insulin dosing for these patients. This is because PA results in increased glucose uptake by muscles and increased insulin sensitivity (higher glucose uptake with the same amount of insulin) that may lead to glycemic imbalance if there is a lack of proper hepatic and pancreatic regulation, which is the case in T1D.

In addition to this, changes in treatment behavior related to PA also contribute to differences in glycemic control. The main sources of glycemic changes due to daily PA in patients with T1D are behavioral and non-behavioral. These are interdependent under suboptimal, open loop glycemic control conditions since patients need to respond to physiological changes by adjusting food intake, insulin injection, and PA adjustments. Patient behavior can also result in physiological changes (e.g., increased glucose uptake during and following PA).

Although PA has widely been demonstrated to decrease HbA1c levels and help glycemic control in patients with type 2 diabetes, previous studies could not provide enough evidence for such improvement in T1D. In addition to the well-known glycemic imbalance caused by structured exercise, recent studies have shown that even light unstructured PA has a significant effect on reducing post meal BG in health and in T1D.

T1D is a chronic disease that results from a lack of endogenous insulin production. Like most chronic diseases, management of diabetes mellitus type 1 (T1D) requires regular monitoring to adjust treatment specifics (e.g. insulin administration, meal regimen) and to avoid long term complications. Complications may occur due to both high and low BG levels. While short term complications for high BG include thirst, tiredness, dizziness and nausea, long term complications range from increased risk of cardiovascular diseases to kidney damage, nerve damage, retina damage.

Low BG levels must be treated as soon as possible since they may lead to seizure, loss of conscious and even to death if left untreated.

Keeping BG levels under control is a challenge encountered recurrently, which necessitates frequent monitoring of BG levels and taking into account as many factors as possible that affect the BG system (i.e. physical activity, stress, ingested meal composition, medications, hormonal changes). The multifactorial nature of the BG system and unpredictable external influences make optimum control hard to achieve and maintain for patients with T1D.

Known strategies to help better management of BG before, during and after an exercise bout (which is a specific case of PA that is performed with the intention of maintaining or improving physical fitness) have many shortcomings. Two exemplary shortcomings of known strategies can be summarized as follows: (1) they focus on BG management related to structured exercise bouts as opposed to unstructured or total daily PA; and (2) there is a trade-off between (i) the strategies that are simple to use, flexible enough to adapt to differing conditions but yield low performance and (ii) the strategies that yield high performance through very precise, patient-specific suggestions but are difficult to use in everyday life.

The present disclosure provides techniques for overcoming shortcomings of known strategies.

BACKGROUND REFERENCES

The following patents, applications and publications as listed below and throughout this document are hereby incorporated herein by reference in their entireties and are not admitted to be prior art with respect to the present disclosure by inclusion herein:

[1]. Colberg, S. R. et al. Physical Activity/Exercise and Diabetes: A Position Statement of the American Diabetes Association. Diabetes Care 39, 2065-2079 (2016).

[2.] Chimen, M. et al. What are the health benefits of physical activity in type 1 diabetes mellitus? A literature review. Diabetologia 55, 542-551 (2012).

[3.] Lack of Glucagon Response to Hypoglycemia in Diabetes: Evidence for an Intrinsic Pancreatic Alpha Cell Defect|Science.

[4.] McMahon, S. K. et al. Glucose Requirements to Maintain Euglycemia after Moderate-Intensity Afternoon Exercise in Adolescents with Type 1 Diabetes Are Increased in a Biphasic Manner. J. Clin. Endocrinol. Metab. 92, 963-968 (2007).

[5.] Marliss, E. B. & Vranic, M. Intense Exercise Has Unique Effects on Both Insulin 30 Release and Its Roles in Glucoregulation. Diabetes 51, S271-S283 (2002).

[6.] MacDonald, M. J. Postexercise Late-Onset Hypoglycemia in Insulin-Dependent Diabetic Patients. Diabetes Care 10, 584-588 (1987).

[7.] Maran, A. et al. Continuous Glucose Monitoring Reveals Delayed Nocturnal Hypoglycemia After Intermittent High-Intensity Exercise in Nontrained Patients with Type 1 Diabetes. Diabetes Technol. Ther. 12, 763-768 (2010).

[8.] Warburton, D. E. R., Nicol, C. W. & Bredin, S. S. D. Health benefits of physical activity: the evidence. Can. Med. Assoc. J. 174, 801-809 (2006).

[9.] Glucose Transporters and Insulin Action—Implications for Insulin Resistance and Diabetes Mellitus—NEJM.

[10.] Brazeau, A.-S., Rabasa-Lhoret, R., Strychar, I. & Mircescu, H. Barriers to Physical Activity Among Patients With Type 1 Diabetes. Diabetes Care 31, 2108-2109 (2008).

[11.] Howorka, K. Functional Insulin Treatment: Principles, Teaching Approach and Practice. (Springer Science & Business Media, 2012).

[12.] Clarke, W. & Kovatchev, B. Statistical Tools to Analyze Continuous Glucose Monitor Data. Diabetes Technol. Ther. 11, S-45 (2009).

The following patents, applications and publications as listed below and throughout this document are hereby incorporated herein by reference in their entireties. It should be appreciated that various aspects of embodiments of the present methods, systems, devices, articles of manufacture, computer readable media, and compositions may be implemented with the following methods, systems, devices, articles of manufacture, computer readable media, and compositions disclosed in the following U.S. Patent Applications, U.S. Patents, and PCT International Patent Applications all of which are hereby incorporated herein by reference in their entireties and co-owned with the assignee, none of which are admitted to be prior art with respect to the present disclosure by inclusion herein:

A. U.S. patent application Ser. No. 15/580,935 entitled "INSULIN MONITORING AND DELIVERY SYSTEM AND METHOD FOR CGM BASED FAULT DETECTION AND MITIGATON VIA METABOLIC STATE TRACKING", filed Dec. 8, 2017.

B. International Patent Application No. PCT/US2016/036729 entitled "INSULIN MONITORING AND DELIVERY SYSTEM AND METHOD FOR CGM BASED FAULT DETECTION AND MITIGATON VIA METABOLIC STATE TRACKING", filed Jun. 9, 2016; Publication No. WO 2016/201120, Dec. 15, 2016.

C. U.S. patent application Ser. No. 15/580,915 entitled "System and Method for Tracking Changes in Average Glycemia in Diabetics", filed Dec. 8, 2017.

D. International Patent Application No. PCT/US2016/5 036481 entitled "System and Method for Tracking Changes in Average Glycemia in Diabetics", filed Jun. 8, 2016; Publication No. WO2016200970, Dec. 15, 2016.

E. U.S. patent application Ser. No. 15/551,503 entitled "Method, System and Computer Readable Medium for Assessing Actionable Glycemic Risk", filed Aug. 16, 2017; Publication No. US-2018-0020988-A1, Jan. 25, 2018.

F. International Patent Application No. PCT/US2016/018027 entitled "Method, System and Computer Readable Medium for Assessing Actionable Glycemic Risk", filed Feb. 16, 2016; Publication No. WO 2016/133879, Aug. 25, 2016.

G. U.S. patent application Ser. No. 15/669,111 entitled "METHOD, SYSTEM AND COMPUTER PROGRAM PRODUCT FOR CGM-BASED PREVENTION OF HYPOGLYCEMIA VIA HYPOGLYCEMIA RISK ASSESSMENT AND SMOOTH REDUCTION INSULIN DELIVERY", filed Aug. 4, 2017; Publication No. US-2017-0337348-A1, Nov. 23, 2017.

H. U.S. patent application Ser. No. 14/015,831 entitled "CGM-Based Prevention of Hypoglycemia Via Hypoglycemia Risk Assessment and Smooth Reduction of Insulin Delivery", filed Aug. 30, 2013; U.S. Pat. No. 9,750,438, issued Sep. 5, 2017.

I. U.S. patent application Ser. No. 13/203,469 entitled "CGM-Based Prevention of Hypoglycemia via Hypoglycemia Risk Assessment and Smooth Reduction Insulin Delivery", filed Aug. 25, 2011; U.S. Pat. No. 8,562,587, issued Oct. 22, 2013.

J. International Patent Application No. PCT/US2010/025405 entitled "CGM-BASED PREVENTION OF HYPOGLYCEMIA VIA HYPOGLYCEMIA RISK ASSESSMENT AND SMOOTH REDUCTION INSULIN DELIVERY", filed Feb. 25, 2010; Publication No. WO 2010/099313 A1, Sep. 2, 2010.

K. International Patent Application No. PCT/US2017/030052 entitled "METHOD, SYSTEM AND APPARATUS FOR REMOTE PATIENT MONITORING OR TRACKING OF SEPSIS-RELATED INDICATORS", filed Apr. 28, 2017; Publication No. WO 2017/189957, Nov. 2, 2017.

L. International Patent Application No. PCT/US2017/015616 entitled "METHOD, SYSTEM, AND COMPUTER READABLE MEDIUM FOR VIRTUALIZATION OF A CONTINUOUS GLUCOSE MONITORING 5 TRACE", filed Jan. 30, 2017; Publication No. WO 2017/132663, Aug. 3, 2017.

M. International Patent Application No. PCT/US2016/058234 entitled "System, Method and Computer Readable Medium for Dynamical Tracking of the Risk for Hypoglycemia in Type 1 and Type 2 Diabetes", filed Oct. 21, 2016; Publication No. WO 2017/070553, Apr. 27, 2017.

N. International Patent Application No. PCT/US2016/054200 entitled "GAIT PATHOLOGY DETECTION AND MONITORING SYSTEM, AND METHOD", filed Sep. 28, 2016; Publication No. WO 2017/058927, Apr. 6, 2017.

O. U.S. patent application Ser. No. 15/255,828 entitled "SYSTEM, METHOD, AND COMPUTER READABLE MEDIUM FOR DYNAMIC INSULIN SENSITIVITY IN DIABETIC PUMP USERS", filed Sep. 2, 2016; Publication No. US-2017-0056591-A1, Mar. 2, 2017.

P. International Patent Application No. PCT/US2016/050109 entitled "SYSTEM, METHOD, AND COMPUTER READABLE MEDIUM FOR DYNAMIC INSULIN SENSITIVITY IN DIABETIC PUMP USERS", filed Sep. 2, 2016; Publication No. WO 2017/040927, Mar. 9, 2017.

Q. U.S. patent application Ser. No. 15/252,365 entitled "Method, System and Computer Readable Medium for Predictive Hypoglycemia Detection for Mild to Moderate Exercise", filed Aug. 31, 2016.

R. U.S. patent application Ser. No. 14/902,731 entitled "SIMULATION OF ENDOGENOUS AND EXOGENOUS GLUCOSE/INSULIN/GLUCAGON INTERPLAY IN TYPE 1 DIABETIC PATIENTS", filed Jan. 4, 2016; Publication No. US-2016-0171183-A1, Jun. 16, 2016.

S. International Patent Application No. PCT/US2014/045393 entitled "SIMULATION OF ENDOGENOUS AND EXOGENOUS GLUCOSE/INSULIN/GLUCAGON INTERPLAY IN TYPE 1 DIABETIC PATIENTS", filed Jul. 3, 2014; Publication No. WO2015003124, Jan. 8, 2015.

T. U.S. patent application Ser. No. 14/769,638 entitled "METHOD AND SYSTEM FOR MODEL-BASED TRACKING OF CHANGES IN AVERAGE GLYCEMIA IN DIABETES", filed Aug. 21, 2015; Publication No. US-2016-0004813-A1, Jan. 7, 2016.

U. International Patent Application No. PCT/US2014/017754 entitled "METHOD AND SYSTEM FOR MODEL-BASED TRACKING OF CHANGES IN AVERAGE GLYCEMIA IN DIABETES", filed Feb. 21, 2014; Publication No. WO 2014/130841, Aug. 28, 2014.

V. U.S. patent application Ser. No. 14/419,375 entitled "COMPUTER SIMULATION FOR TESTING AND MONITORING OF TREATMENT STRATEGIES FOR STRESS HYPERGLYCEMIA", filed Feb. 3, 2015; Publication No. 2015-0193589, Jul. 9, 2015.

W. International Patent Application No. PCT/US2013/053664 entitled "COMPUTER SIMULATION FOR TESTING AND MONITORING OF TREATMENT STRATEGIES FOR STRESS HYPERGLYCEMIA", filed Aug. 5, 2013; Publication No. WO 2014/022864, Feb. 6, 2014.

X. U.S. patent application Ser. No. 14/266,612 entitled "Method, System and Computer Program Product for Real-Time Detection of Sensitivity Decline in Analyte Sensors", filed Apr. 30, 2014; U.S. Pat. No. 9,882,660, issued Jan. 30, 2018.

Y. U.S. patent application Ser. No. 13/418,305 entitled "Method, System and Computer Program Product for Real-Time Detection of Sensitivity Decline in Analyte Sensors", filed Mar. 12, 2012; U.S. Pat. No. 8,718,958, issued May 6, 2014.

Z. U.S. patent application Ser. No. 11/925,689 entitled "Method, System and Computer Program Product for Real-Time Detection of Sensitivity Decline in Analyte Sensors", filed Oct. 26, 2007; U.S. Pat. No. 8,135,548, issued Mar. 13, 2012.

AA. International Patent Application No. PCT/US2007/082744 entitled "Method, System and Computer Program Product for Real-Time Detection of Sensitivity Decline in Analyte Sensors", filed Oct. 26, 2007; Publication No. WO/2008/052199, May 2, 2008.

BB. U.S. patent application Ser. No. 14/241,383 entitled "Method, System and Computer Readable Medium for Adaptive Advisory Control of Diabetes", filed Feb. 26, 2014; Publication No. 2015-0190098, Jul. 9, 2015.

CC. International Patent Application No. PCT/US2012/052422 entitled "Method, System and Computer Readable Medium for Adaptive 5 Advisory Control of Diabetes", filed Aug. 26, 2012; Publication No. WO 2013/032965, Mar. 7, 2013.

DD. U.S. patent application Ser. No. 14/128,922 entitled "Unified Platform For Monitoring and Control of Blood Glucose Levels in Diabetic Patients", filed Dec. 23, 2013; Publication No. 2015/0018633, Jan. 15, 2015.

EE. International Patent Application No. PCT/US2012/043910 entitled "Unified Platform For Monitoring and Control of Blood Glucose Levels in Diabetic Patients", filed Jun. 23, 2012; Publication No. WO 2012/178134, Dec. 27, 2012.

FF. U.S. patent application Ser. No. 14/128,811 entitled "Methods and Apparatus for Modular Power Management and Protection of Critical Services in Ambulatory Medical Devices", filed Dec. 23, 2013; U.S. Pat. No. 9,430,022, issued Aug. 30, 2016.

GG. International Patent Application No. PCT/US2012/043883 entitled "Methods and Apparatus for Modular Power Management and Protection of Critical Services in Ambulatory Medical Devices", filed Jun. 22, 2012; Publication No. WO 2012/178113, Dec. 27, 2012.

HH. U.S. patent application Ser. No. 13/637,359 entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES", filed Sep. 25, 2012; U.S. Pat. No. 9,398,869, issued Jul. 26, 2016.

II. International Patent Application No. PCT/US2011/029793 entitled "METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES", filed Mar. 24, 2011; Publication No. WO 2011/119832, Sep. 29, 2011.

JJ. U.S. patent application Ser. No. 13/634,040 entitled "Method and System for the Safety, Analysis, and Supervision of Insulin Pump Action and Other Modes of Insulin Delivery in Diabetes", filed Sep. 11, 2012; Publication No. 2013/0116649, May 9, 2013.

KK. International Patent Application No. PCT/US2011/028163 entitled "Method and System for the Safety, Analysis, and Supervision of Insulin Pump Action and Other Modes of Insulin Delivery in Diabetes", filed Mar. 11, 2011; Publication No. WO 2011/112974, Sep. 15, 2011.

LL. U.S. patent application Ser. No. 13/394,091 entitled "Tracking the Probability for Imminent Hypoglycemia in Diabetes from Self-Monitoring Blood Glucose (SMBG) Data", filed Mar. 2, 2012; Publication No. 2012/0191361, Jul. 26, 2012.

MM. International Patent Application No. PCT/US2010/047711 entitled "Tracking the Probability for Imminent Hypoglycemia in Diabetes from Self-Monitoring Blood Glucose (SMBG) Data", filed Sep. 2, 2010; Publication No. WO 2011/028925, Mar. 10, 2011.

NN. U.S. patent application Ser. No. 13/322,943 entitled "System Coordinator and Modular Architecture for Open-Loop and Closed-Loop Control of Diabetes", filed Nov. 29, 2011; Publication No. 2012/0078067, Mar. 29, 2012.

OO. International Patent Application No. PCT/US2010/036629 entitled "System Coordinator and Modular Architecture for Open-Loop and Closed-Loop Control of Diabetes", filed May 28, 2010; Publication No. WO 2010/138848, Dec. 2, 2010.

PP. U.S. patent application Ser. No. 13/131,467 entitled "Method, System, and Computer Program Product for Tracking of Blood Glucose Variability in Diabetes", filed May 26, 2011; U.S. Pat. No. 9,317,657, issued Apr. 19, 2016.

QQ. International Patent Application No. PCT/US2009/065725 entitled "Method, System, and Computer Program Product for Tracking of Blood Glucose Variability in Diabetes", filed Nov. 24, 2009; Publication No. WO 2010/062898, Jun. 3, 2010.

RR. U.S. patent application Ser. No. 12/674,348 entitled "Method, Computer Program Product and System for Individual Assessment of Alcohol Sensitivity", filed Feb. 19, 2010; Publication No. 2011/0264374, Oct. 27, 2011.

SS. International Patent Application No. PCT/US2008/073738 entitled "Method, Computer Program Product and System for Individual Assessment of Alcohol Sensitivity", filed Aug. 20, 2008; Publication No. WO 2009/026381, Feb. 26, 2009.

TT. U.S. patent application Ser. No. 12/665,420 entitled "LQG Artificial Pancreas Control System and Related Method", filed Dec. 18, 2009; Publication No. 2010/0249561, Sep. 30, 2010.

UU. International Patent Application No. PCT/US2008/067723 entitled "LQG Artificial Pancreas Control System and Related Method", filed Jun. 20, 2008; Publication No. WO 2008/157780, Dec. 24, 2008.

VV. U.S. patent application Ser. No. 12/665,149 entitled "Method, System and Computer Program Product for Evaluation of Insulin Sensitivity, Insulin/Carbohydrate Ratio, and Insulin Correction Factors in Diabetes from Self-Monitoring Data", filed Dec. 17, 2009; Publication No. 2010/0198520, Aug. 5, 2010.

WW. International Patent Application No. PCT/US2008/069416 entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008; Publication No. WO 2009/009528, Jan. 15, 2009.

XX. U.S. patent application Ser. No. 12/664,444 entitled "Method, System and Computer Simulation Environment for Testing of Monitoring and Control Strategies in Diabetes", filed Dec. 14, 2009; Publication No. 2010/0179768, Jul. 15, 2010.

YY. International Patent Application No. PCT/US2008/067725 entitled "Method, System and Computer Simulation Environment for Testing of Monitoring and Control Strategies in Diabetes", filed Jun. 20, 2008; Publication No. WO 2008/157781, Dec. 24, 2008.

ZZ. U.S. patent application Ser. No. 12/516,044 entitled "Method, System, and Computer Program Product for the Detection of Physical Activity by Changes in Heart Rate, Assessment of Fast Changing Metabolic States, and Applications of Closed and Open Control Loop in Diabetes", filed May 22, 2009; U.S. Pat. No. 8,585,593, issued Nov. 19, 2013.

AAA. International Patent Application No. PCT/US2007/085588 entitled "Method, System, and Computer Program Product for the Detection of Physical Activity by Changes in Heart Rate, Assessment of Fast Changing Metabolic States, and Applications of Closed and Open Control Loop in Diabetes", filed Nov. 27, 2007; Publication No. WO2008/067284, Jun. 5, 2008.

SUMMARY

A computer-implemented method for treating a patient suffering from T1D is disclosed. The method includes quantifying physical activity (PA) of the patient; calculating an accumulated PA periodically based on the quantified PA, the accumulated PA indicating an aggregate of the PA; and generating an activity informed insulin bolus by adjusting a prevalent functional insulin therapy bolus with a previous activity component, wherein the previous activity component is based on the accumulated daily PA, an activity profile, and an activity factor of the patient.

A system for treating a patient suffering from T1D is disclosed. The system includes a quantifying module configured to quantify PA of the patient; an accumulation module configured to calculate an accumulated PA periodically based on the quantified PA, the accumulated PA indicating an aggregate of the PA; a generation module configured to generate an activity informed insulin bolus by adjusting a prevalent functional insulin therapy bolus with a previous activity component, wherein the previous activity component is based on the accumulated daily PA, an activity profile, and an activity factor of the patient; and a dosing device configured to administer the activity informed insulin bolus.

A computer-implemented method for treating a patient suffering from T1D is disclosed. The method includes determining an additional glucose uptake within a time period, the additional glucose uptake being caused by a PA; translating the additional glucose uptake into a number of insulin units with a same BG lowering impact; and generating an exercise informed insulin bolus by adjusting a prevalent functional insulin therapy bolus with the insulin units.

A system for treating a patient suffering from T1D is disclosed. The system includes a determination module configured to determine an additional glucose uptake within a time period, the additional glucose uptake being caused by a PA; a translation module configured to translate the additional glucose uptake into a number of insulin units with a same BG lowering impact; a generation module configured to generate an exercise informed insulin bolus by adjusting a prevalent functional insulin therapy bolus with the insulin units; and a dosing device configured to administer the activity informed insulin bolus.

BRIEF DESCRIPTION OF THE DRAWINGS

Other objects and advantages of the present disclosure will become apparent to those skilled in the art upon reading the following detailed description of exemplary embodiments, in conjunction with the accompanying drawings, in which like reference numerals have been used to designate like elements, and in which.

DETAILED DESCRIPTION

Figure 1:
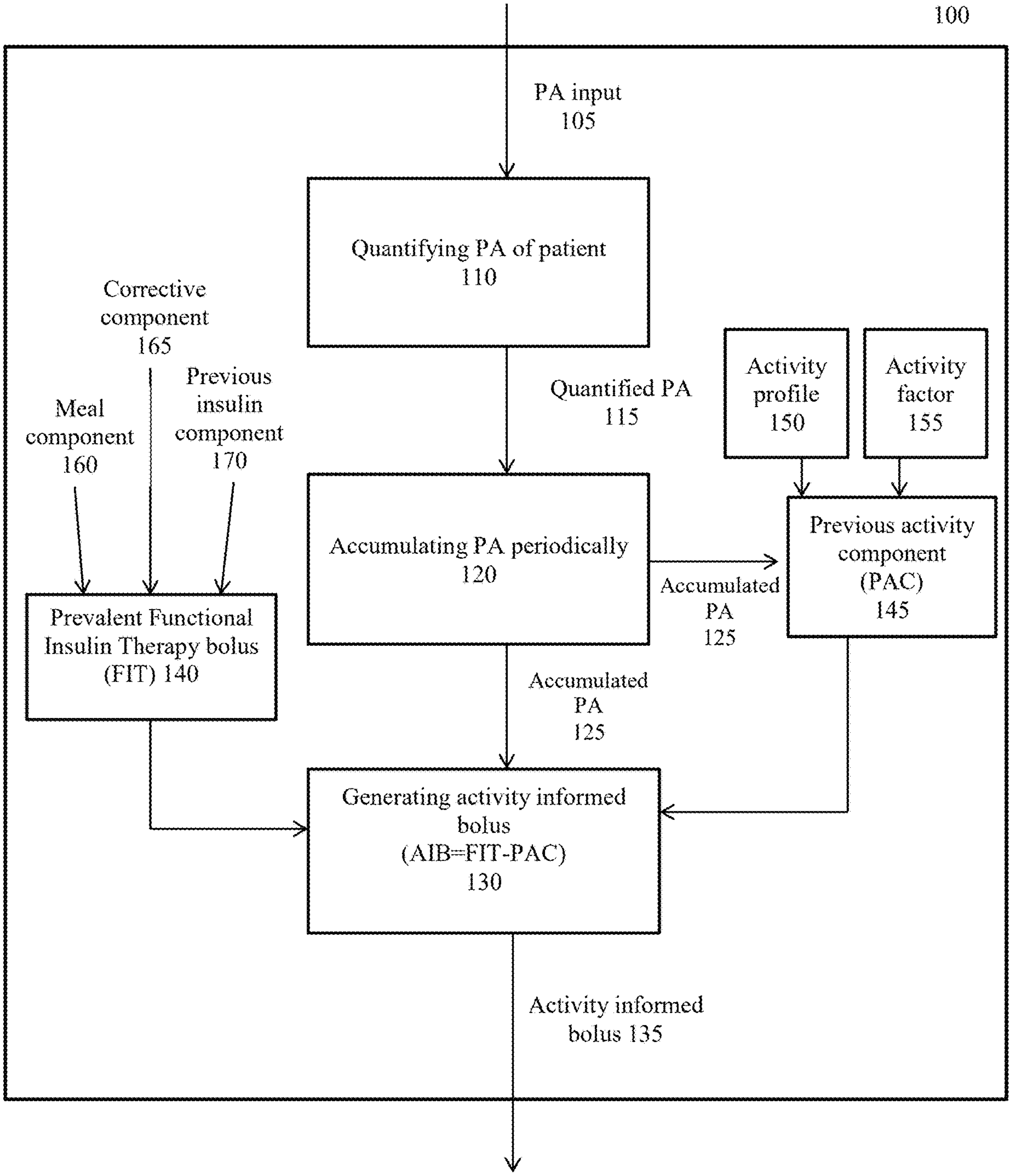
FIG. 1 illustrates a flowchart for an exemplary computer-implemented method for treating a patient suffering from T1D.

The present disclosure provides a decision support method and system that includes PA related insulin bolus adjustments in daily treatment of T1D that can yield a better glucose management. FIG. 1 illustrates a flowchart for an exemplary computer-implemented method 100 for treating a patient suffering from T1D. In an exemplary embodiment, the method 100 can include a step 110 of quantifying physical activity (PA) 115 of the patient. PA 105 can be obtained by different techniques. For example, PA can be obtained by an input that includes measuring heart rate, a time period when a patient is active, and/or a daily step count, or any equivalents thereof. A wearable or non-wearable PA tracker, such as a pedometer that provides PA data at frequent intervals can be used as a measurement device for measuring the PA. The measurement device can provide step count, heart rate, calories burned and/or distance traveled as PA quantifiers. A patient's daily PA profile can be extracted from PA data collected for a duration that is sufficient to capture patterns in a patient's daily PA.

In an exemplary embodiment, step count obtained from a pedometer, or any equivalents thereof, can be used for quantifying PA. In some cases, step count can be easy to collect in daily life and less subject to change based on a person's health status than calories burned and heart rate information. Specifically, calories burned can be a rough approximation by a pedometer and can be different even for people of the same age, sex, height and weight according to their metabolic state and body composition. As for the heart rate, its variation may be caused by various factors other than physical activity (e.g., medications, psychological stress, fear, hormonal changes, and hypoglycemia). However, a step count is not affected by any of these inter and intra person differences and is ubiquitously available in daily life (even PA tracker applications on smart phones provide step count data).

In an exemplary embodiment, the method 100 can include a step 120 of calculating an accumulated PA 125 periodically based on the quantified PA 115. The accumulated PA 125 can be calculated at a time of bolus calculation for the patient. An index called as activity on board (AOB) can be used to define the PA accumulated from previous hours that has an impact on blood glucose (BG) uptake. AOB can be calculated as a weighted sum of PA recorded over time where the time window and weights for activity at each time interval are obtained from an activity clearance curve. AOB can be obtained for different time windows preceding the time for which it's calculated. $AOB_t = AI_{1xn} \times W_{nx1}$, where: AOB: Activity on Board; t: the time when AOB is calculated; n: number of previous instances that contribute to $AOB_t$; AI: activity indicator vector; and W: weight vector that is obtained from activity clearance curve.

Figure 2:
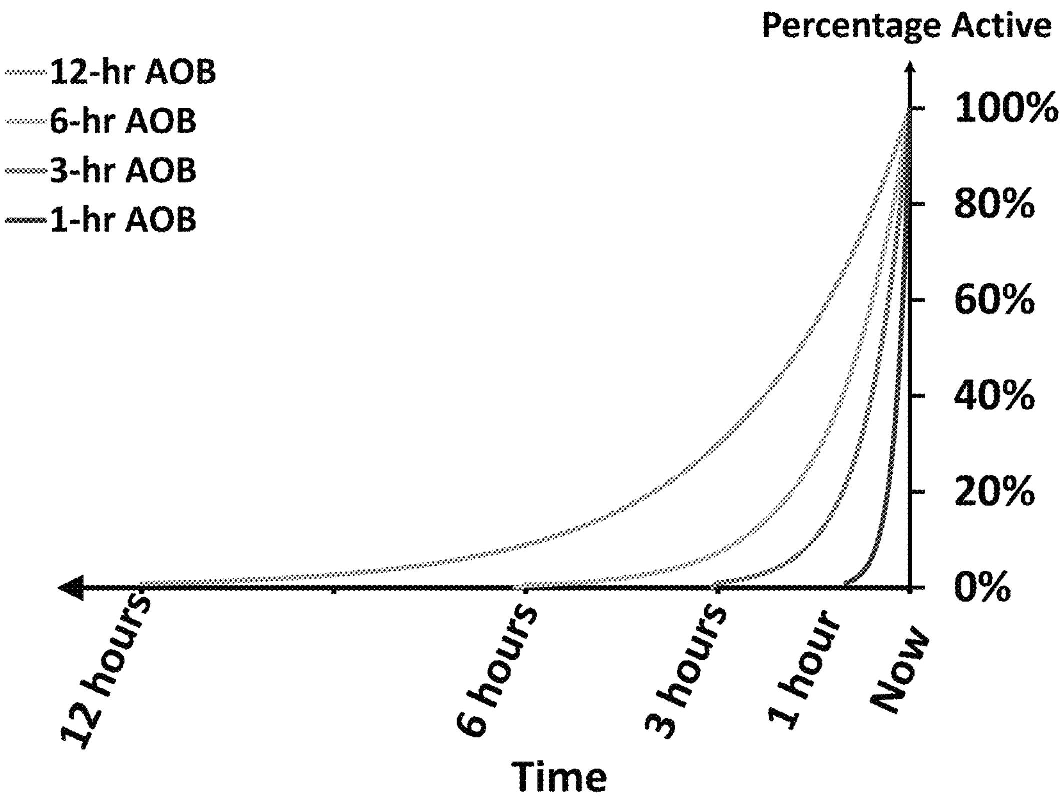
FIG. 2 shows an exemplary exponential activity clearance curve.
Figure 3:
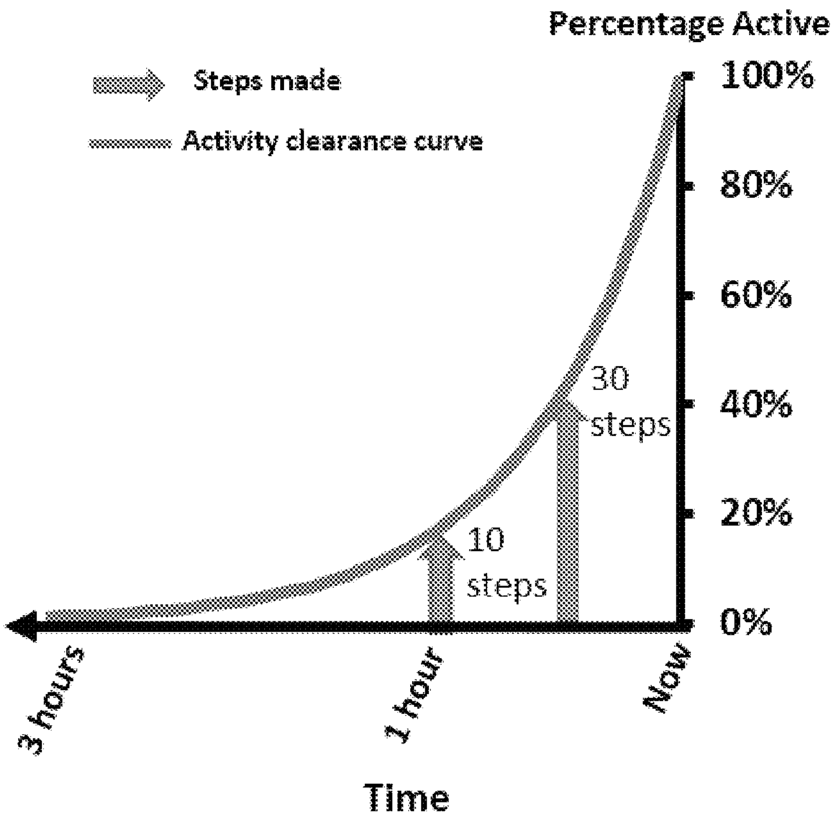
FIG. 3 is an exemplary illustration of AOB calculated by convolving step count impulses with the AOB curve.
Figure 4:
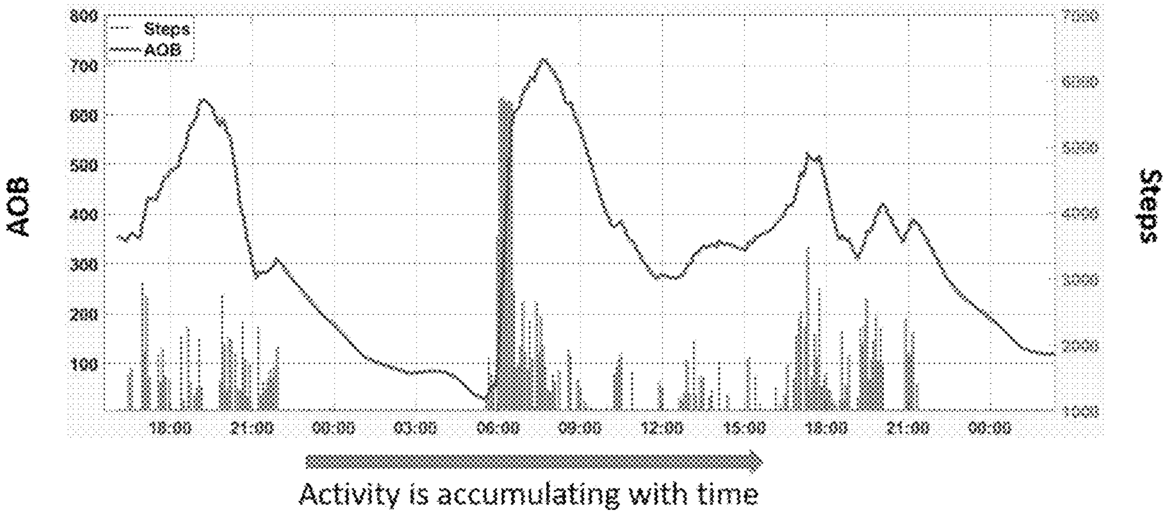
FIG. 4 is an exemplary illustration of AOB calculation by convolving step count impulses with the AOB curve.

FIG. 2 shows an exemplary exponential activity clearance curves for PA within the 1, 3, 6, and 12 hours window preceding the time of the AOB calculation. FIG. 3 shows a sample representation of AOB calculation by use of historical step input and an activity clearance curve. $AOB_{Now}$=30 steps×40%+10 steps×20%=14. FIG. 4 is an exemplary illustration of AOB calculated by convolving step count impulses with the AOB curve.

In an exemplary embodiment, the method 100 can include a step 130 of generating an activity informed insulin bolus 135 by adjusting a prevalent functional insulin therapy bolus 140 with a previous activity component 145, wherein the previous activity component 145 is based on the accumulated daily PA 125, an activity profile 150, and an activity factor 155 of the patient.

In an exemplary embodiment, the prevalent functional insulin therapy bolus 140 can be based on a meal component 160, a correction component 165, and a previous insulin component 170. The functional insulin therapy bolus 140 can be calculated based on the below formula, referenced in S. Schmidt and K. Nørgaard, "Bolus Calculators", J. Diabetes Sci. Technol., vol. 8, no. 5, pp. 1035-1041, September 2014. See also Cappon, Giacomo, et al. "In Silico Assessment of Literature Insulin Bolus Calculation Methods Accounting for Glucose Rate of Change." Journal of diabetes science and technology 13.1 (2019): 103-110.

$$FIT\ \text{Bolus}_t = \underbrace{\frac{BG_t - \text{Target } BG}{\text{Correction Factor}}}_{\text{Correction component}} + \underbrace{\frac{\text{Estimated Carbohydrate Intake}_t}{\text{Carbohydrate Ratio}}}_{\text{Meal component}} - \underbrace{\text{Insulin On Board}_t}_{\text{Previous insulin component}}$$

Figure 5:
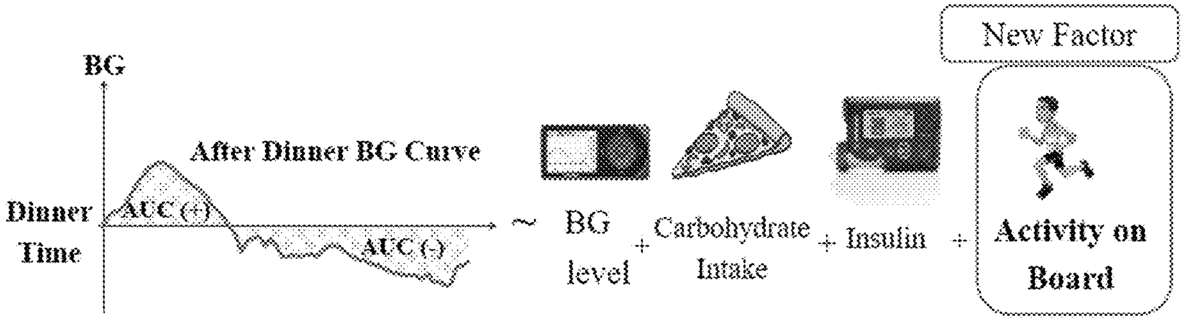
FIG. 5 is an exemplary illustration of the regression model used to evaluate the effect of AOB on post dinner glycemic excursion.

FIG. 5 shows an exemplary regression model to examine the impact of AOB on after meal glycemic response in addition to the other factors currently used in meal bolus calculation (i.e. BG level, amount of carbohydrate in the meal, insulin that has previously injected and still has an impact on glycemia) by assessing glucose area under postprandial curve (AUC). This area is associated with the CGM value at the meal time, the amount of carbohydrates ingested and the amount of insulin in the blood stream. Therefore, these variables form the core variables of the present regression models. The impact of previous PA captured by AOB is explored by evaluating its statistical significance when it is added to these regression models.

In an exemplary embodiment, the meal component 160 can be based on a ratio of an estimated carbohydrate intake and an amount of carbohydrate compensated by one unit of insulin. The meal component 160 can be the insulin required to cover the glycemic increase from the carbohydrates (CHO) in the current meal to be treated. The Carbohydrate Ratio (CR) can be the amount of CHO that is compensated for by 1 unit of insulin. The meal component 160 can be obtained from a meal input information that can indicate an amount of carbohydrates (CHO) in the current meal to be dosed which is estimated by the patient.

In an exemplary embodiment, the correction component 165 can be based on current blood glucose (BG), target BG, and a correction factor that indicates a decrease in BG resulting from a single unit of the insulin. The current BG can be the monitored BG value at a time of bolus decision and the target BG can be reference glucose level desired for optimal treatment, which can be based on an insulin history that provides information to avoid insulin overdosing and it is kept track of by some insulin injection devices (e.g. insulin pumps, smart insulin pens), or by the patient. The correction component 165 can be the insulin required to compensate for the difference between target and current BG level when the BG is higher than the target. The correction Factor (CF) can be the decrease in the BG resulting from 1 unit of insulin injection.

In an exemplary embodiment, the previous insulin component 170 can be based on insulin that is in circulation due to previous insulin injections. The previous insulin component 170 can be insulin on board (IOB) that is the active insulin in circulation due to previous insulin injections but has not completed its action yet.

In an exemplary embodiment, the treatment parameters used in the functional insulin therapy bolus 140 calculation (i.e. the CR, CF and target BG) can be determined by the patient's physician and can have an impact on the BG control performance. Other than the treatment parameters, the performance of the glucose control is highly impacted by the amount and timing of insulin injections—which is decided by the patient in the open loop system.

Good glucose control requires keeping BG levels in target range with a low variability for the highest possible amount of time. Target range for BG levels is between 70 mg/dl and 180 mg/dl (this can also be expressed in mmol/L units as 2.9 mmol/L and 10 mmol/L respectively). When BG levels are below 70 mg/dl, the person is hypoglycemic and when they are above 180 mg/dl, they are hyperglycemic. During hypoglycemia, patients treat themselves by ingesting food or drinks that increase BG levels quickly (e.g. orange juice). For hyperglycemia, patients treat themselves by injecting insulin. Like any drug, over or under dosing of insulin leads to problems. Over-dosing is likely to result in like hypoglycemia and under-dosing may provoke hyperglycemia.

There are different types of insulin analogues that address different needs and are used in insulin injection processes. Some examples of insulin are as follows. Rapid-acting insulin: taken prandially or as a correction bolus, and used with a longer-acting insulin to keep BG levels in control outside of the meal horizon. Also, this is the type of insulin that can be used in insulin pumps. Short acting insulin used to cover BG rising effect of meal. It needs to be injected 30 minutes before the meal, and is used with longer-acting insulin to keep BG levels in control outside of the time of meals. Intermediate-acting: longer acting compared to the rapid and shorting acting counterparts. It helps keeping BG under control with a lifetime of about half a day and can be taken twice a day. Long-acting: taken to keep BG under control for 12 to 24 hours and can be accompanied by rapid or short acting insulin for meal times. These are synthetically-made insulins that are analogous of human insulin. There is also synthetic human insulin manufactured by placing the DNA code for making insulin into bacteria or yeast cells.

In an exemplary embodiment, the activity profile 150 can be determined by calculating a median of an accumulated daily PA measured at a specific time of a day for multiple days. The activity profile 150 can characterize a patient's regular activity. In an exemplary embodiment, the method 100 can include a step of taking extra action for any deviations from the activity profile, that are expected to result in higher glycemic risk unless they are compensated.

Figure 6:
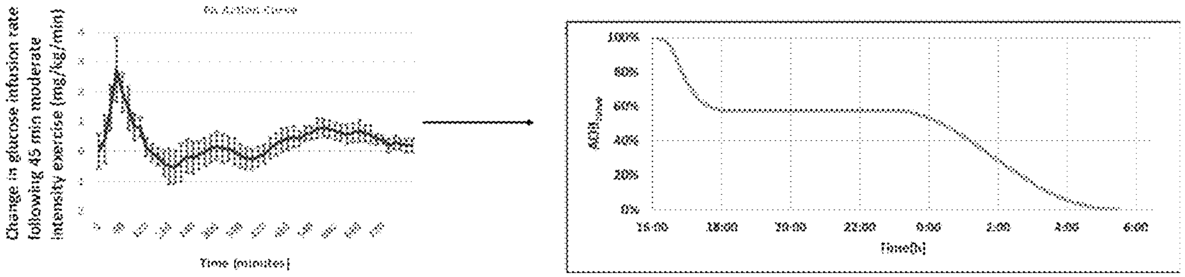
FIG. 6 illustrates an exemplary PA clearance curve obtained from a PA action curve.

In an exemplary embodiment, the activity profile 150 can be determined based on an accumulated PA, and AOB, by convolving the step count impulses with a PA clearance curve (activity on board curve). The clearance curves can be altered from simple exponential curves to ones that include a biphasic impact based on McMahon et al.'s study, incorporate by reference (S. K. McMahon et al., "Glucose Requirements to Maintain Euglycemia after Moderate-Intensity Afternoon Exercise in Adolescents with Type 1 Diabetes Are Increased in a Biphasic Manner," J. Clin. Endocrinol. Metab., vol. 92, no. 3, pp. 963-968, March 2007.). Since this study provides a 12-hour glycemic response to PA, the glucose infusion rate curve can be used as the PA action curve to obtain a PA clearance curve through the formula immediately below, and illustrated in FIG. 6.

$$\text{Activity on Board Curve } [t_1] = 1 - \frac{\sum_{t=0}^{t_1} PA \text{ action curve}[t]}{\sum_{t=0}^{T} PA \text{ action curve}[t]}$$

Figure 7:
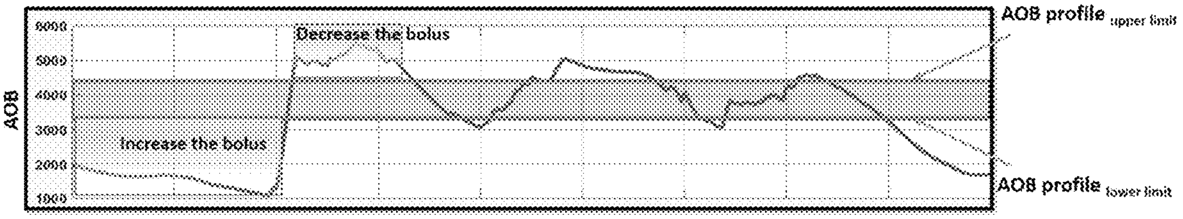
FIG. 7 illustrates an exemplary AOB profile empirically defined around the median of AOB observed at dinner times.

In an exemplary embodiment, the activity profile 150 can be extracted for the dinner time. The activity profile can be calculated as the median of the AOB at the dinner time across all of the patient's available days of data. A band of AOB in which there would be no PA-related insulin adjustment can be defined. This band can be empirically chosen as the area between the median of the AOB at the dinner time and one absolute deviation (1MAD) below this median. FIG. 7 illustrates an AOB profile empirically defined around the median of AOB observed at dinner times for a patient.

When the AOB at dinner time is above this band, the insulin dose can be decreased to compensate for the expected higher glucose uptake caused by additional PA. When the AOB at dinner time is below the band, the insulin dose can be increased to compensate for the expected lower glucose uptake caused by the lack of PA compared to the AOB profile. The decision of how much insulin needs to be added or subtracted can be made based on the activity factor 155.

In an exemplary embodiment, the activity factor 155 can be determined by calculating an amount of the accumulated PA that has a same impact on BG of the patient as a single unit of insulin. The Activity Factor (AF) 155, can be used as the control gain and its value is obtained by an optimization procedure. It corresponds to the amount of AOB that has equivalent glycemic impact to one unit of insulin and it is a patient-specific parameter, similar to a carbohydrate ratio and correction factor which is used in a functional insulin therapy. The AF 155 can be obtained for each patient as the value that yields the optimal BG control when PA informed bolus treatment is applied to minimize total glycemic risk.

In an exemplary embodiment, the steps for developing PA informed bolus treatment strategy can be as follows: 1) calculation of accumulated activity (as previously described); 2) extraction of activity profile and defining bands of action based on the activity profile (as previously described); 3) obtaining a balanced CR around the activity profile; and 4) analysis of postprandial glucose excursions using the PA integrated bolus calculator to find the AF that results in optimal BG control in the hours following dinner.

In an exemplary embodiment, optimal BG can be obtained by an optimization procedure that includes carbohydrate ratio (CR) optimization. CR can be an important element for a mealtime bolus. A patient's CR can be optimized across all days to obtain the best postprandial glucose control that CR alterations alone may yield within the activity profile band.

In an exemplary embodiment, the best postprandial glucose control can be defined as the control that yields the minimum average total glycemic risk (hypoglycemic risk+hyperglycemic risk) in the post-dinner phase. The glycemic risk can be calculated according to the journal article B. P. Kovatchev, M. Straume, D. J. Cox, and L. S. Farhy, "Risk Analysis of Blood Glucose Data: A Quantitative Approach to Optimizing the Control of Insulin Dependent Diabetes," Computational and Mathematical Methods in Medicine, 2000, incorporated here by reference.

In an exemplary embodiment, to obtain a CR that is optimum in the activity profile band and allows for PA related corrections out of this band, optimization can be performed by weighing in and out of the band cases differently. The objective function can assign higher penalty to the risk associated with low BG for cases of AOB below the action band. It can also assign higher penalty to the risk associated with high BG for cases of AOB above the action band. The allowed sub-optimality in the out of action band can be corrected by AF. An exemplary function using a CR optimization process is shown below.

$$\text{argmin}_{CR}\ \text{Total cost} = \sum_{d=1}^{\#\,of\,days} \text{Total Balanced } BG \text{ Risk}_d$$

For d = 1: total # of days

If ($AOB_{dinner\ time}$ > AOB high $\text{profile}_{dinner\ time}$)

$\alpha = 0.65$;

$$\text{Balanced High } BG \text{ Risk}_d = \alpha \cdot \text{High } BG \text{ risk}_d \cdot \frac{AOB_{dinner\ time}}{AOB \text{ high profile}_{dinner\ time}};$$

$$\text{Balanced Low } BG \text{ Risk}_d = (1-\alpha) \cdot \text{Low } BG \text{ risk}_d \cdot \frac{AOB \text{ low profile}_{dinner\ time}}{AOB_{dinner\ time}};$$

Elseif ($AOB_{dinner\ time}$ < AOB low $\text{profile}_{dinner\ time}$)

$\alpha = 0.65$;

$$\text{Balanced High } BG \text{ Risk}_d = (1-\alpha) \cdot \text{High } BG \text{ risk}_d \cdot \frac{AOB_{dinner\ time}}{AOB \text{ low profile}_{dinner\ time}};$$

$$\text{Balanced Low } BG \text{ Risk}_d = \alpha \cdot \text{Low } BG \text{ risk}_d \cdot \frac{AOB \text{ high profile}_{dinner\ time}}{AOB_{dinner\ time}};$$

Else $\alpha = 0.5$;

Balanced High BG $\text{Risk}_d = \alpha \cdot$ High BG $\text{risk}_d$;

Balanced Low BG $\text{Risk}_d = (1 - \alpha) \cdot$ Low BG $\text{risk}_d$;

End

Total Balanced BG $\text{Risk}_d$ = Balanced High BG $\text{Risk}_d$ + Balanced Low BG $\text{Risk}_d$;

End

In an exemplary embodiment, AF optimization can include obtaining an optimum AF pair for PA related insulin adjustments—AF1 to be used when the accumulated PA is higher than the activity profile and AF2 to be used when it is below the profile. The optimum AF pair can be obtained after obtaining an activity profile and an optimum CR that provides sufficient control within the activity profile band. An exemplary cost function to obtain the AF couple that would yield the optimum glycemic control is shown below.

$$\text{argmin}_{AF_1, AF_2} \sum_{d=1}^{d=\#of\,days} (\text{Total } BG \text{ Risk}_d)$$

Net effect simulator can be used to "replay" CGMs and obtain AFs that provides minimum glycemic risk with the present PA-informed treatment method for each patient, as described in the reference: "D. Patek et al., "Empirical Representation of Blood Glucose Variability in a Compartmental Model," in Prediction Methods for Blood Glucose Concentration, Springer, Cham, 2016, pp. 133-157.

Figure 8:
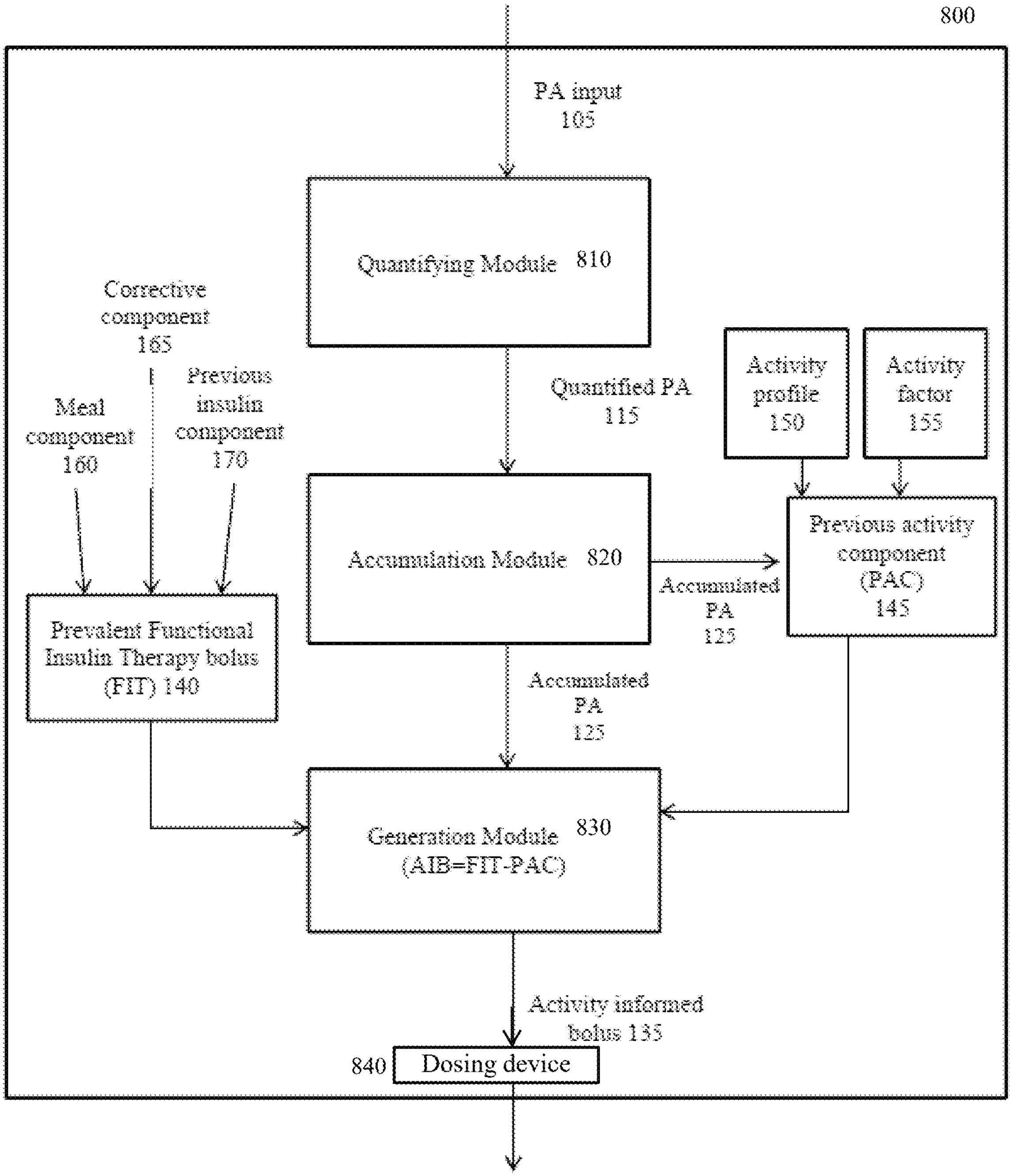
FIG. 8 is an exemplary diagram of a system for treating a patient suffering from T1D.

FIG. 8 illustrates an exemplary system 800 for treating a patient suffering from T1D. In an exemplary embodiment, the system 800 can include a quantifying module 810 configured to quantify PA of the patient based on the previously described step 110 of the method 100. In an exemplary embodiment, the system 800 can include an accumulation module 820 configured to quantify PA of the patient based on the previously described step 120 of the method 100. In an exemplary embodiment, the system 800 can include a generation module 830 configured to generate an activity informed insulin bolus of the patient based on the previously described step 130 of the method 100. In an exemplary embodiment, the system 800 can include a dosing device 840 configured to administer the activity informed insulin bolus.

In an exemplary embodiment, the system 800 can be "open loop" control which, in this context, means that the feedback between monitoring and control (i.e., insulin injection) devices happens only when the patient checks the glucose value manually and use this information in their treatment decisions. In an exemplary embodiment, the system 800 can also be used in closed loop system. Any combination of monitoring and insulin injection devices can be used based on patient preferences and their healthcare team's suggestions.

Figure 9:
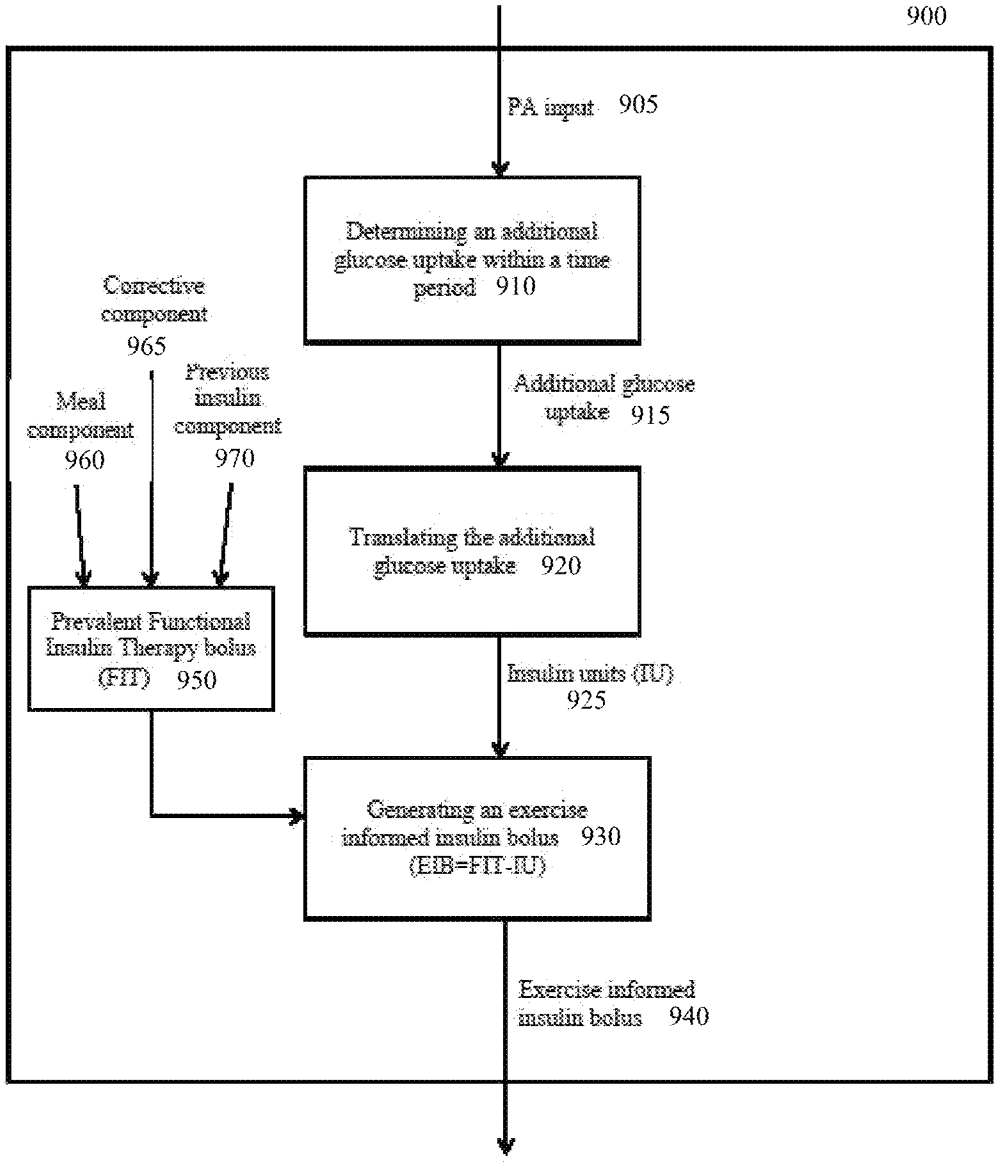
FIG. 9 illustrates a flowchart for an exemplary computer-implemented method for treating a patient suffering from T1D.

FIG. 9 illustrates a flowchart for an exemplary computer-implemented method 900 for treating a patient suffering from T1D. In an exemplary embodiment, the method 900 can include a step 910 of determining an additional glucose uptake within a time period, the additional glucose uptake 915 being caused by a PA 905. The time period can be duration of insulin action (DIA) for a bolus is the time that takes for an injected insulin bolus to clear out from the blood circulation.

In an exemplary embodiment, a PA action curve can be used to calculate the additional glucose uptake 915 in grams for a patient's body weight (BW) within the interval of insulin action ($\Delta GU_{DIA}$).

$$\Delta GU_{DIA} = \sum_{k=\text{Time of the bolus}}^{\text{Time of the bolus}+DIA} \frac{w_k * BW}{1000}$$

Figure 10:
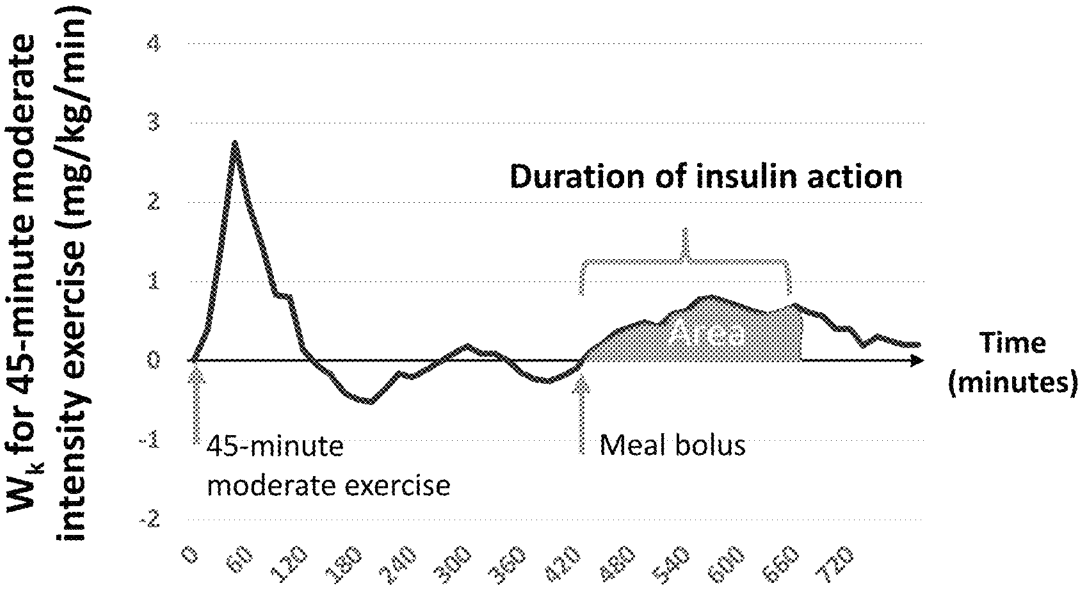
FIG. 10 illustrates an exemplary calculation of estimated exercise induced total change in the glucose uptake per kilogram body weight within the duration of an insulin action by use of a signal $w_k$ generated from a 45-minute moderate exercise.

FIG. 10 illustrates a calculation of an exercise induced total estimated change in the glucose uptake per kilogram body weight within the duration of insulin action of a meal bolus. It is indicated by the highlighted area and $\Delta GU_{DIA}$ is obtained by multiplying this area with the patient's BW/1000. The highlighted area is obtained through the signal $w_k$. This signal corresponds to the exercise induced change in the glucose uptake per kilogram body weight per minute and is in mg/kg/min units. In this example, it is generated by a 45-minute moderate intensity exercise.

Figure 11:
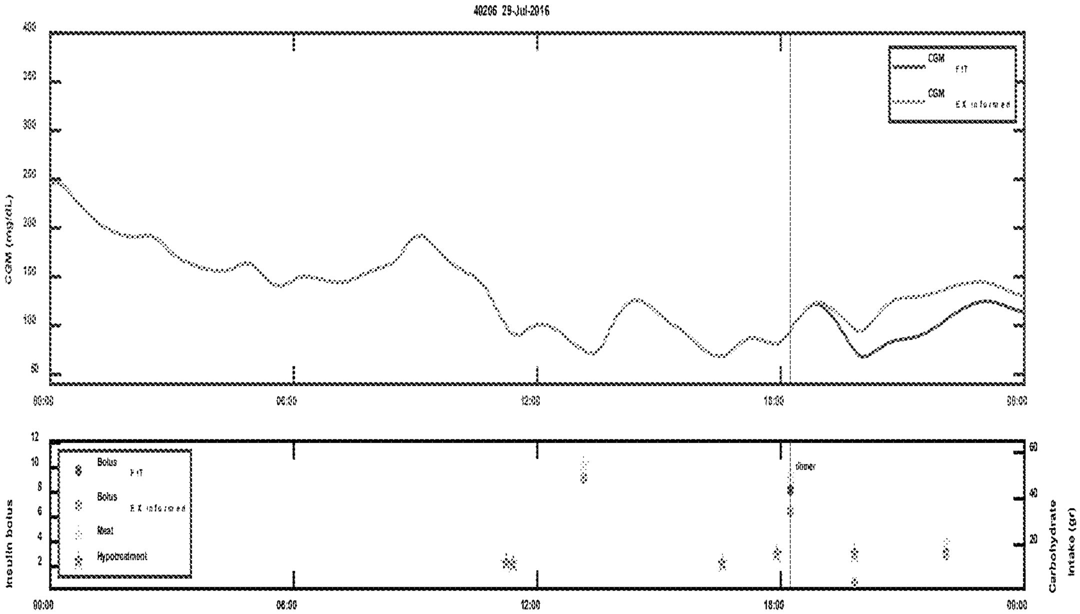
FIG. 11 is an exemplary graph showing a comparison of CGM associated with functional insulin therapy and CGM associated with exercise informed bolus.

FIG. 11 is an exemplary graph showing a comparison of CGM associated with functional insulin therapy and CGM associated with exercise informed bolus. Exercise informed bolus can be adjusted the bolus according to the anticipated exercise induced increase in glucose uptake following dinner time. The decrease in the bolus by exercise informed bolus can prevent the steep glucose drop seen when the FIT bolus is administered.

As shown in FIG. 11, a patient performs 45-minutes moderate intensity exercise at 11 am and eats dinner at 6:14 pm. Bolus at the dinnertime is 8.19 units when calculated according to FIT formula. The patient weighs 90.7 kg, her insulin to carbohydrate ratio is 1 unit per 6 gr of carbohydrate and duration of insulin action (DIA) is chosen as 4 hours. Using $w_k$ that corresponds to the signal of estimated change in the glucose uptake rate due the performed exercise, the total anticipated change in the glucose uptake is calculated within the interval of insulin action ($\Delta GU_{DIA}$) as follows:

$$\Delta GU_{DIA} = \sum_{k=\text{Time of dinner bolus}}^{\text{Time of the bolus}+DIA} \frac{w_k * BW}{1000}$$

-continued $$\Delta GU_{DIA} = \sum_{k=6:14\,pm}^{10:14\,pm} \frac{w_k * 90.7}{1000} = 10.5 \text{ gr}$$

In an exemplary embodiment, the patient's CR at dinner time can be used to calculate the exercise related correction component by translating $\Delta GU_{DIA}$ into insulin units through dividing $\Delta GU_{DIA}$ by CR. This calculation yields a 1.75 unit of adjustment and adjusted dinnertime insulin becomes 6.44 units.

In an exemplary embodiment, the method 900 can include a step 920 of translating the additional glucose uptake into insulin units 925 with a same BG lowering impact. The translating can be performed by dividing $\Delta GU_{DIA}$ by a carbohydrate ratio (CR). In an exemplary embodiment, the method 900 can include a step 930 of generating an exercise informed insulin bolus 940 by adjusting a prevalent functional insulin therapy bolus 950 with the insulin units 925. In an exemplary embodiment, the functional insulin therapy bolus 950 can be calculated in a similar manner as previously described in step 140. The adjusting can be performed by subtracting a ratio of $\Delta GU_{DIA}$ and CR from the prevalent functional insulin therapy bolus, as shown in the formula below.

$$\text{Exercise Informed Bolus}_t = \frac{CHO\ \text{Intake}_t}{CR} + \frac{BG_t - BG_{target}}{CF} - IOB_t - \frac{\Delta GU_{DIA}}{CR}$$

Figure 12:
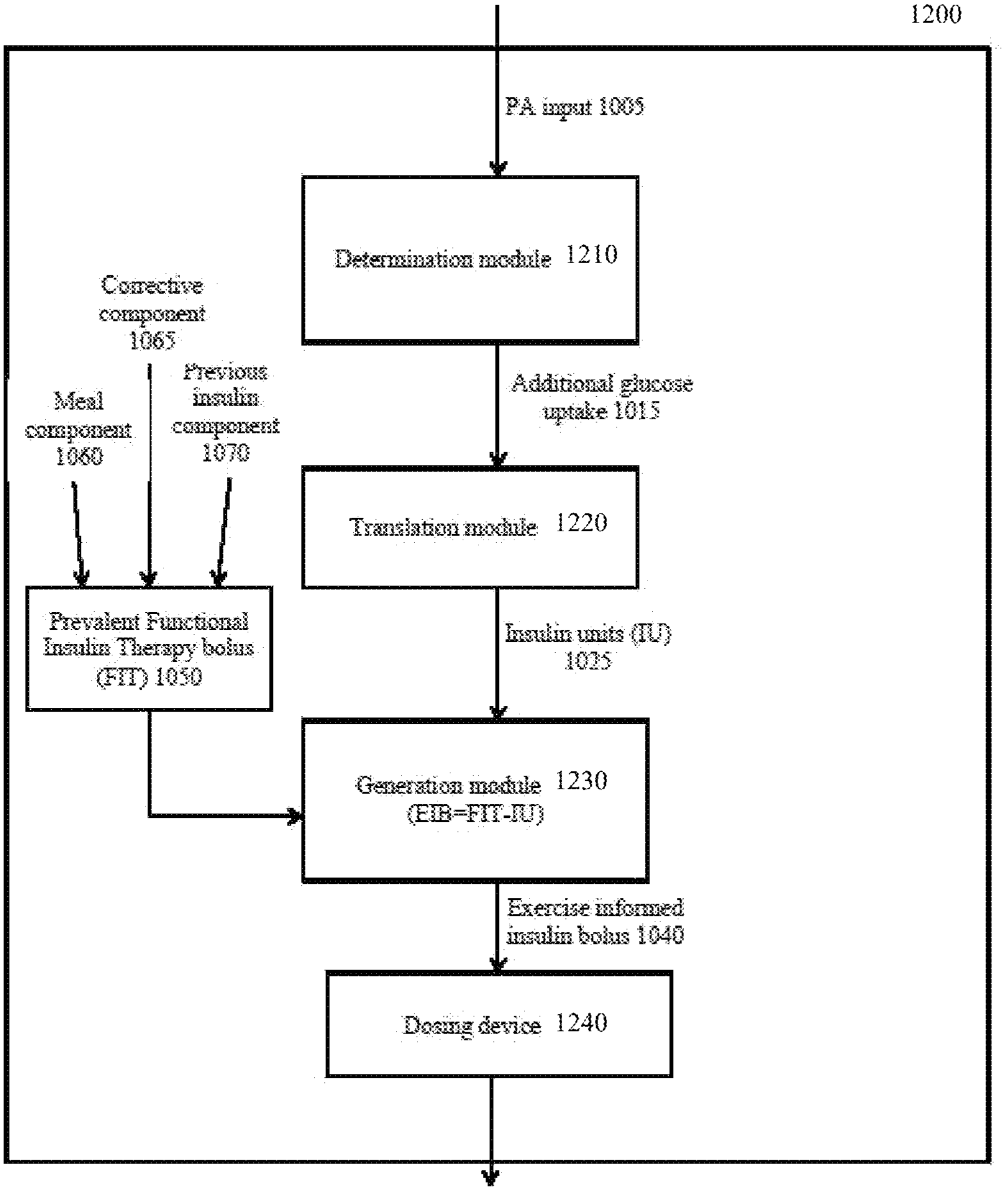
FIG. 12 is an exemplary diagram for a system for treating a patient suffering from T1D.

FIG. 12 shows an exemplary system 1200 for treating a patient suffering from T1D. In an exemplary embodiment, the system 1200 can include a determination module 1210 configured to determine an additional glucose uptake 915 within a time period based on the previously described step 910 of the method 900. In an exemplary embodiment, the system 1200 can include a translation module 1220 configured to translate the additional glucose uptake 915 into insulin units 925 with a same BG lowering impact based on the previously described step 920 of the method 900. In an exemplary embodiment, the system 1200 can include a generation module 1230 configured to generate an exercise informed insulin bolus 940 of the patient by adjusting a prevalent functional insulin therapy bolus 950 with the insulin units 925 as described in step 930 of the method 900. In an exemplary embodiment, the system 1200 can include a dosing device 1240 configured to administer the exercise informed insulin bolus 940.

In an exemplary embodiment, the system 1200 can be "open loop" control which, in this context, means that the feedback between monitoring and control (i.e., insulin injection) devices happens only when the patient checks the glucose value manually and use this information in their treatment decisions. In an exemplary embodiment, the system 1200 can also be used in closed loop system. Any combination of monitoring and insulin injection devices can be used based on patient preferences and their healthcare team's suggestions.

Figure 13A:
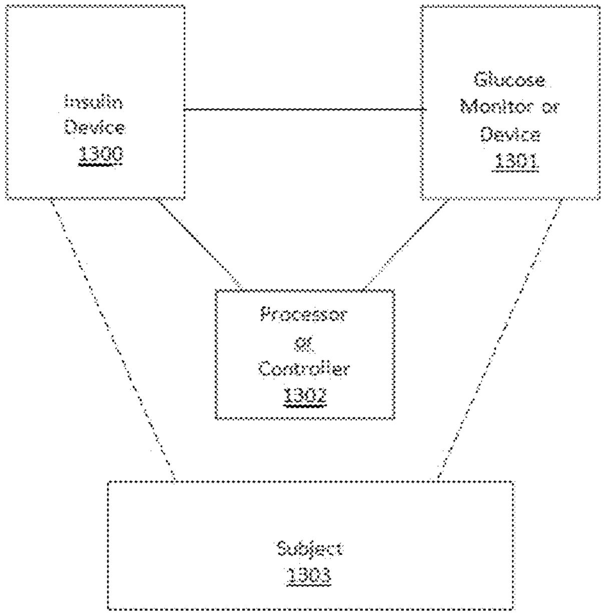
FIG. 13A is an exemplary high level functional block diagram of an embodiment of the present disclosure.

FIG. 13A is a high level functional block diagram of an exemplary embodiment, or an aspect of an embodiment. A processor or controller 1302 communicates with the glucose monitor or device 1301 (e.g. dosing device 840, 1240), and optionally the insulin device 1300. The glucose monitor or device 1301 communicates with the subject 1303 to monitor glucose levels of the subject 1303. The processor or controller 1302 is configured to perform the desired calculations. Optionally, the insulin device 1300 communicates with the subject 1303 to deliver insulin to the subject 1303. The processor or controller 1302 is configured to perform the required calculations. The glucose monitor 1301 and the insulin device 1300 may be implemented as a separate device or as a single device. The processor 1302 can be implemented locally in the glucose monitor 1301, the insulin device 1300, or a standalone device (or in any combination of two or more of the glucose monitor, insulin device, or a stand along device). The processor 1302 or a portion of the system can be located remotely such that the device is operated as a telemedicine device.

Figure 13B:
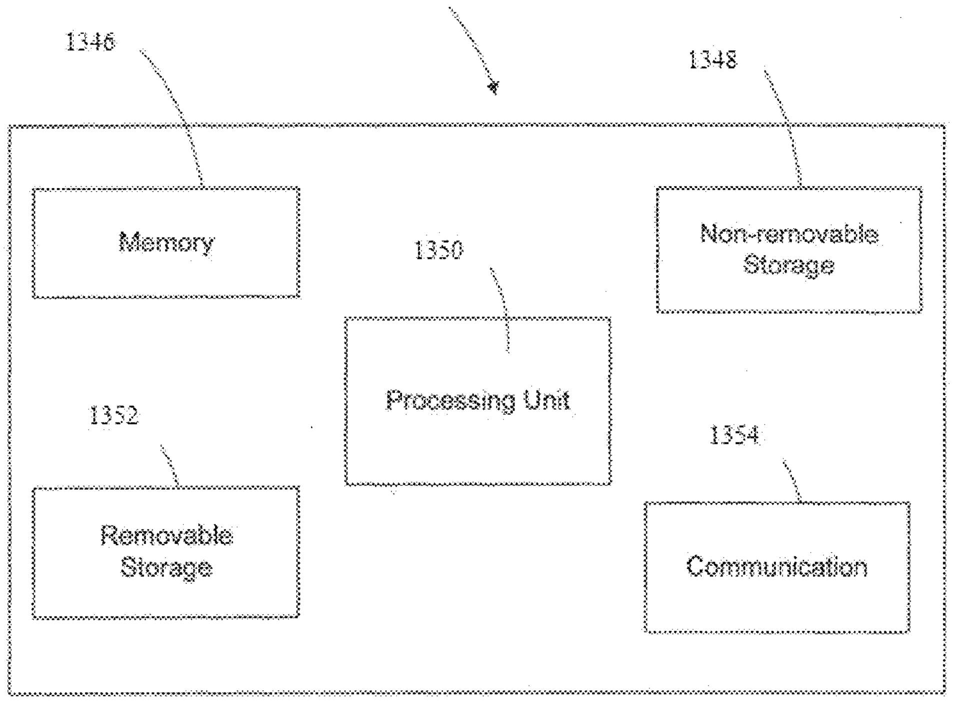
FIG. 13B illustrates an exemplary computing device in which embodiments of the present disclosure can be implemented.

FIG. 13B, in its most basic configuration, illustrates a computing device 1344 with at least one processing unit 1350 and memory 1346. Depending on the exact configuration and type of computing device, memory 1346 can be volatile (such as RAM), nonvolatile (such as ROM, flash memory, etc.) or some combination of the two.

Additionally, device 1344 may also have other features and/or functionality. For example, the device could also include additional removable and/or non-removable storage including, but not limited to, magnetic or optical disks or tape, as well as writable electrical storage media. Such additional storage is shown in FIG. 13B by removable storage 1352 and non-removable storage 1348. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology CDROM, digital versatile disks (DVD) or other optical storage, magnetic cassettes, magnetic tape, magnetic disk storage or other magnetic storage devices, or any other medium which can be used to store the desired information and which can accessed by the device. Any such computer storage media may be part of, or used in conjunction with, the device.

The device may also contain one or more communications connections 1354 that allow the device to communicate with other devices (e.g., other computing devices). The communications connections carry information in a communication media. Communication media can embody computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode, execute, or process information in the signal. By way of example, and not limitation, communication medium includes wired media such as a wired network or direct-wired connection, and wireless media such as radio, RF, infrared and other wireless media. As discussed above, the term computer readable media as used herein includes both storage media and communication media.

In addition to a stand-alone computing machine, exemplary embodiments can also be implemented on a network system having a plurality of computing devices that are in communication with a networking means, such as a network with an infrastructure or an ad hoc network. The network connection can be wired connections or wireless connections.

Figure 14A:
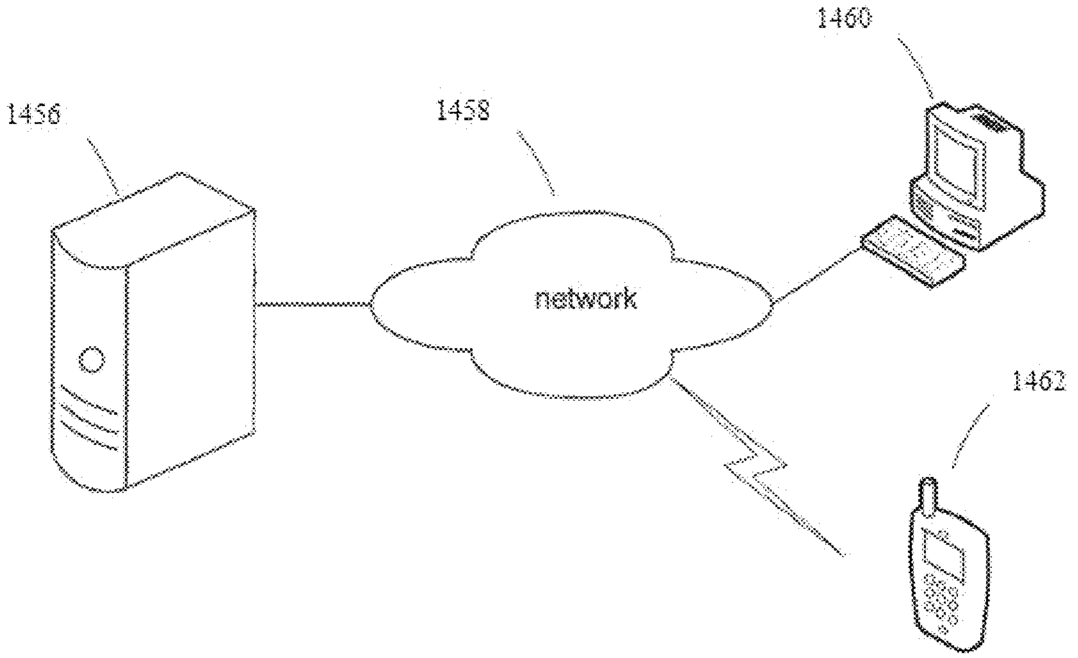
FIG. 14A illustrates an exemplary network system in which embodiments of the present disclosure can be implemented.

FIG. 14A illustrates a network system in which embodiments can be implemented. In this example, the network system includes computer 1456 (e.g. a network server), network connection means 1458 (e.g. wired and/or wireless connections), computer terminal 1460, and PDA (e.g. a smart-phone) 1462 (or other handheld or portable device, such as a cell phone, laptop computer, tablet computer, GPS receiver, mp3 player, handheld video player, pocket projector, etc. or handheld devices (or non-portable devices) with combinations of such features). In an embodiment, it should be appreciated that the module listed as 1456 may be glucose monitor device. In an embodiment, it should be appreciated that the module listed as 1456 may be a glucose monitor device and/or an insulin device.

Any of the components shown or discussed with FIG. 14A may be multiple in number. The embodiments can be implemented in anyone of the devices of the system. For example, execution of the instructions or other desired processing can be performed on the same computing device that is any one of 1456, 1460, and 1462. Alternatively, an embodiment can be performed on different computing devices of the network system. For example, certain desired or required processing or execution can be performed on one of the computing devices of the network (e.g. server 1456 and/or glucose monitor device), whereas other processing and execution of the instruction can be performed at another computing device (e.g. terminal 1460) of the network system, or vice versa. Certain processing or execution can be performed at one computing device (e.g. server 1456 and/or glucose monitor device); and the other processing or execution of the instructions can be performed at different computing devices that may or may not be networked.

For example, the certain processing can be performed at terminal 1460, while the other processing or instructions are passed to device 1462 where the instructions are executed. This scenario may be of particular value especially when the PDA 1462 device, for example, accesses to the network through computer terminal 1460 (or an access point in an ad hoc network). For another example, software to be protected can be executed, encoded or processed with one or more embodiments. The processed, encoded or executed software can then be distributed to customers. The distribution can be in a form of storage media (e.g. disk) or electronic copy.

Figure 14B:
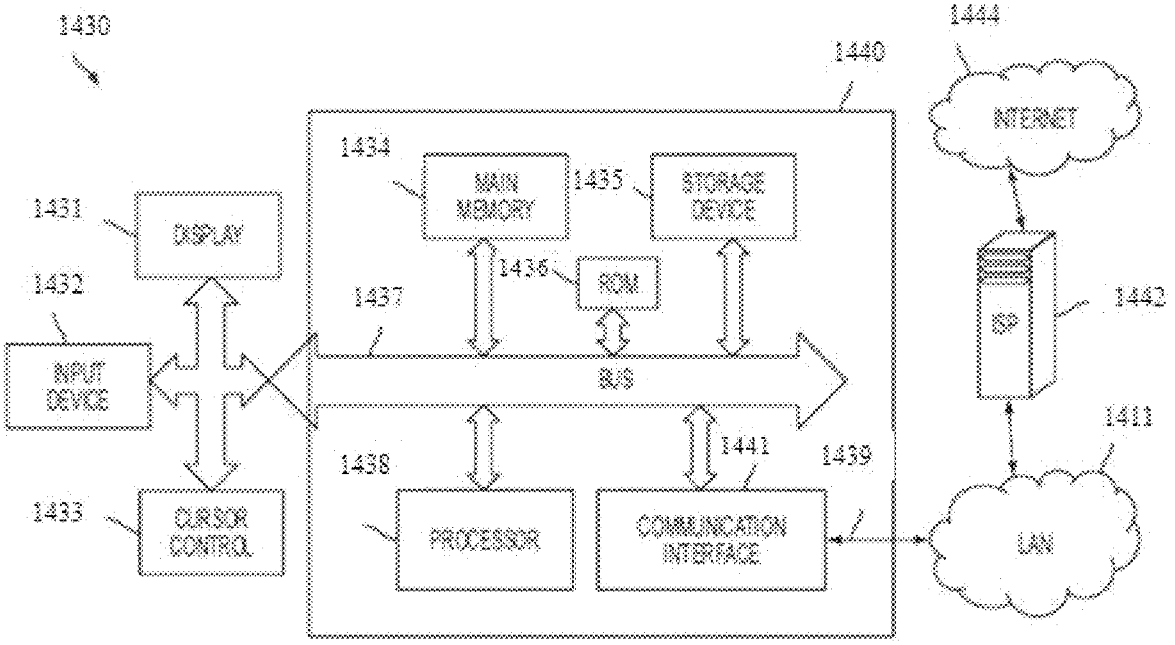
FIG. 14B is an exemplary block diagram that illustrates a system including a computer system and the associated Internet connection upon which an embodiment may be implemented.

FIG. 14B is a block diagram that illustrates a system 1430 including a computer system 1440 and the associated Internet 1444 connection upon which an embodiment may be implemented. Such configuration can be used for computers (hosts) connected to the Internet 1444 and executing a server or a client (or a combination) software. A source computer such as laptop, an ultimate destination computer and relay servers, for example, as well as any computer or processor described herein, may use the computer system configuration and the Internet connection shown in FIG. 14B. The system 1440 may be used as a portable electronic device such as a notebook/laptop computer, a media player (e.g., MP3 based or video player), a cellular phone, a Personal Digital Assistant (PDA), a glucose monitor device, an insulin delivery device, an image processing device (e.g., a digital camera or video recorder), and/or any other handheld computing devices, or a combination of any of these devices.

Note that while FIG. 14B illustrates various components of an exemplary computer system, it is not intended to represent any particular architecture or manner of interconnecting the components; as such details are not germane to the present disclosure. It will also be appreciated that network computers, handheld computers, cell phones and other data processing systems which have fewer components or perhaps more components may also be used. The computer system of FIG. 14B may, for example, be an Apple Macintosh computer or Power Book, or an IBM compatible PC. Computer system 1440 includes a bus 1437, an interconnect, or other communication mechanism for communicating information, and a processor 1438, commonly in the form of an integrated circuit, coupled with bus 1437 for processing information and for executing the computer executable instructions. Computer system 1440 also includes a main memory 1434, such as a Random Access Memory (RAM) or other dynamic storage device, coupled to bus 1437 for storing information and instructions to be executed by processor 1438.

Main memory 1434 also may be used for storing temporary variables or other intermediate information during execution of instructions to be executed by processor 1438. Computer system 140 further includes a Read Only Memory (ROM) 1436 (or other non-volatile memory) or other static storage device coupled to bus 1437 for storing static information and instructions for processor 1438. A storage device 1435, such as a magnetic disk or optical disk, a hard disk drive for reading from and writing to a hard disk, a magnetic disk drive for reading from and writing to a magnetic disk, and/or an optical disk drive (such as DVD) for reading from and writing to a removable optical disk, is coupled to bus 1437 for storing information and instructions.

The hard disk drive, magnetic disk drive, and optical disk drive may be connected to the system bus by a hard disk drive interface, a magnetic disk drive interface, and an optical disk drive interface, respectively. The drives and their associated computer-readable media provide non-volatile storage of computer readable instructions, data structures, program modules and other data for the general purpose computing devices. Computer system 1440 can include an Operating System (OS) stored in a non-volatile storage for managing the computer resources and provides the applications and programs with an access to the computer resources and interfaces. An operating system commonly processes system data and user input, and responds by allocating and managing tasks and internal system resources, such as controlling and allocating memory, prioritizing system requests, controlling input and output devices, facilitating networking and managing files. Non-limiting examples of operating systems are Microsoft Windows, Mac OS X, and Linux.

The term "processor" is meant to include any integrated circuit or other electronic device (or collection of devices) capable of performing an operation on at least one instruction including, without limitation, Reduced Instruction Set Core (RISC) processors, CISC microprocessors, Microcontroller Units (MCUs), CISC-based Central Processing Units (CPUs), and Digital Signal Processors (DSPs). The hardware of such devices may be integrated onto a single substrate (e.g., silicon "die"), or distributed among two or more substrates. Furthermore, various functional aspects of the processor may be implemented solely as software or firmware associated with the processor.

Computer system 1440 may be coupled via bus 1437 to a display 1431, such as a Cathode Ray Tube (CRT), a Liquid Crystal Display (LCD), a flat screen monitor, a touch screen monitor or similar means for displaying text and graphical data to a user. The display may be connected via a video adapter for supporting the display. The display allows a user to view, enter, and/or edit information that is relevant to the operation of the system. An input device 1432, including alphanumeric and other keys, is coupled to bus 1437 for communicating information and command selections to processor 1438. Another type of user input device is cursor control 1433, such as a mouse, a trackball, or cursor direction keys for communicating direction information and command selections to processor 1438 and for controlling cursor movement on display 1431. This input device can for example have two degrees of freedom in two axes, a first axis (e.g., x) and a second axis (e.g., y), that allows the device to specify positions in a plane.

The computer system 1440 may be used for implementing the methods and techniques described herein. According to an exemplary embodiment, those methods and techniques are performed by computer system 1440 in response to processor 1438 executing one or more sequences of one or more instructions contained in main memory 1434. Such instructions may be read into main memory 1434 from another computer-readable medium, such as storage device 1435. Execution of the sequences of instructions contained in main memory 1434 causes processor 1438 to perform the process steps described herein. In alternative embodiments, hard-wired circuitry may be used in place of or in combination with software instructions to implement the arrangement. Thus, embodiments are not limited to any specific combination of hardware circuitry and software.

The term "computer-readable medium" (or "machine-readable medium") as used herein is an extensible term that refers to any medium or any memory, that participates in providing instructions to a processor, (such as processor 1438) for execution, or any mechanism for storing or transmitting information in a form readable by a machine (e.g., a computer). Such a medium may store computer-executable instructions to be executed by a processing element and/or control logic, and data which is manipulated by a processing element and/or control logic, and may take many forms, including but not limited to, non-volatile medium, volatile medium, and transmission medium. Transmission media includes coaxial cables, copper wire and fiber optics, including the wires that comprise bus 1437. Transmission media can also take the form of acoustic or light waves, such as those generated during radio-wave and infrared data communications, or other form of propagated signals (e.g., carrier waves, infrared signals, digital signals, etc.). Common forms of computer-readable media include, for example, a floppy disk, a flexible disk, hard disk, magnetic tape, or any other magnetic medium, a CD-ROM, any other optical medium, punch-cards, paper-tape, any other physical medium with patterns of holes, a RAM, a PROM, and EPROM, a FLASH-EPROM, any other memory chip or cartridge, a carrier wave as described hereinafter, or any other medium from which a computer can read.

Note that while FIG. 14B illustrates various components of a computer system, it is not intended to represent any particular architecture or manner of interconnecting the components; as such details are not germane to the present disclosure. It will also be appreciated that network computers, handheld computers, cell phones and other data processing systems which have fewer components or perhaps more components may also be used. The computer system of FIG. may, for example, be an Apple Macintosh computer or Power Book, or an IBM compatible PC. Computer system includes a bus, an interconnect, or other communication mechanism for communicating information, and a processor, commonly in the form of an integrated circuit, coupled with bus for processing information and for executing the computer executable instructions. Computer system also includes a main memory, such as a Random Access Memory (RAM) or other dynamic storage device, coupled to bus for storing information and instructions to be executed by a processor.

Various forms of computer-readable media may be involved in carrying one or more sequences of one or more instructions to processor 1438 for execution. For example, the instructions may initially be carried on a magnetic disk of a remote computer. The remote computer can load the instructions into its dynamic memory and send the instructions over a telephone line using a modem. A modem local to computer system 1440 can receive the data on the telephone line and use an infra-red transmitter to convert the data to an infra-red signal. An infra-red detector can receive the data carried in the infra-red signal and appropriate circuitry can place the data on bus 1437. Bus 1437 carries the data to main memory 1434, from which processor 138 retrieves and executes the instructions. The instructions received by main memory 1434 may optionally be stored on storage device 1435 either before or after execution by processor 1438.

Computer system 1440 also includes a communication interface 1441 coupled to bus 1437. Communication interface 1441 provides a two-way data communication coupling to a network link 1439 that is connected to a local network 1411. For example, communication interface 1441 may be an Integrated Services Digital Network (ISDN) card or a modem to provide a data communication connection to a corresponding type of telephone line. As another non-limiting example, communication interface 1441 may be a local area network (LAN) card to provide a data communication connection to a compatible LAN. For example, Ethernet based connection based on IEEE802.3 standard may be used such as 10/100BaseT, 1000BaseT (gigabit Ethernet), 10 gigabit Ethernet (10 GE or 10 GbE or 10 GigE per IEEE Std 802.3ae-2002 as standard), 40 Gigabit Ethernet (40 GbE), or 100 Gigabit Ethernet (100 GbE as per Ethernet standard IEEE P802.3ba), as described in Cisco Systems, Inc. Publication number 1-587005-001-3 (6/99), "Internetworking Technologies Handbook", Chapter 7: "Ethernet Technologies", pages 7-1 to 7-38, which is incorporated in its entirety for all purposes as if fully set forth herein. In such a case, the communication interface 1441 typically include a LAN transceiver or a modem, such as Standard Microsystems Corporation (SMSC) LAN91C111 10/100 Ethernet transceiver described in the Standard Microsystems Corporation (SMSC) data-sheet "LAN91C111 10/100 Non-PCI Ethernet Single Chip MAC+PHY" Data-Sheet, Rev. 15 (02-20-04), which is incorporated in its entirety for all purposes as if fully set forth herein.

Wireless links may also be implemented. In any such implementation, communication interface 1441 sends and receives electrical, electromagnetic or optical signals that carry digital data streams representing various types of information. Network link 1439 typically provides data communication through one or more networks to other data devices. For example, network link 1439 may provide a connection through local network 1411 to a host computer or to data equipment operated by an Internet Service Provider (ISP) 1142. ISP 1442 in turn provides data communication services through the world wide packet data communication network Internet 1444. Local network 1411 and Internet 1444 both use electrical, electromagnetic or optical signals that carry digital data streams. The signals through the various networks and the signals on the network link 1439 and through the communication interface 1441, which carry the digital data to and from computer system 1440, are exemplary forms of carrier waves transporting the information. A received code may be executed by processor 1438 as it is received, and/or stored in storage device 1435, or other non-volatile storage for later execution. In this manner, computer system 1440 may obtain application code in the form of a carrier wave.

Figure 15A:
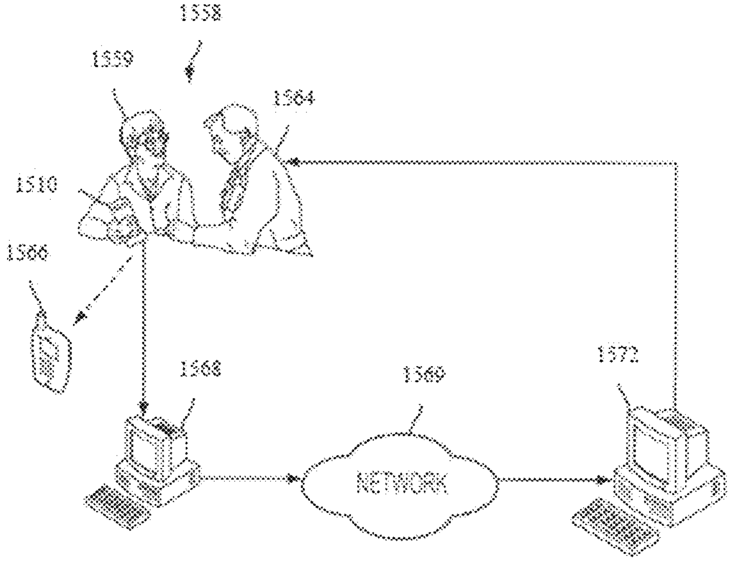
FIG. 15A illustrates an exemplary system in which one or more embodiments of the disclosure can be implemented using a network, or portions of a network or computers.

FIG. 15A illustrates a system in which one or more embodiments can be implemented using a network, or portions of a network or computers, although the present glucose device may be practiced without a network.

In an exemplary embodiment, the glucose monitor may be implemented by the subject (or patient) locally at home or other desired location. However, in an alternate embodiment it may be implemented in a clinic setting or assistance setting. For instance, referring to FIG. 15A, a clinic setup 1558 provides a place for doctors (e.g., 1564) or clinician/assistant to diagnose patients (e.g. 1559) with diseases related with glucose and related diseases and conditions. A glucose monitoring device 1510 can be used to monitor and/or test the glucose levels of the patient—as a standalone device. It should be appreciated that while only glucose monitor device 1510 is shown in the Figure, the system and any component thereof may be used in the manner depicted by FIG. 15A.

The system or component may be affixed to the patient or in communication with the patient as desired or required. For example the system or combination of components thereof—including a glucose monitor device 1510 (or other related devices or systems such as a controller, and/or an insulin pump, or any other desired or required devices or components)—may be in contact, communication or affixed to the patient through tape or tubing (or other medical instruments or components) or may be in communication through wired or wireless connections. Such monitor and/or test can be short term (e.g., clinical visit) or long term (e.g., clinical stay or family). The glucose monitoring device outputs can be used by the doctor (clinician or assistant) for appropriate actions, such as insulin injection or food feeding for the patient, or other appropriate actions or modeling. Alternately, the glucose monitoring device output can be delivered to computer terminal 1568 for instant or future analyses. The delivery can be through cable or wireless or any other suitable medium. The glucose monitoring device output from the patient can also be delivered to a portable device, such as PDA 1566. The glucose monitoring device outputs with improved accuracy can be delivered to a glucose monitoring center 1572 for processing and/or analyzing. Such delivery can be accomplished in many ways, such as network connection 1570, which can be wired or wireless.

In addition to the glucose monitoring device outputs, errors, parameters for accuracy improvements, and any accuracy related information can be delivered, such as to computer 1568, and/or glucose monitoring center 1572 for performing error analyses. This can provide a centralized accuracy monitoring, modeling and/or accuracy enhancement for glucose centers, due to the importance of the glucose sensors. Exemplary embodiments can also be implemented in a standalone computing device associated with the target glucose monitoring device.

Figure 15B:
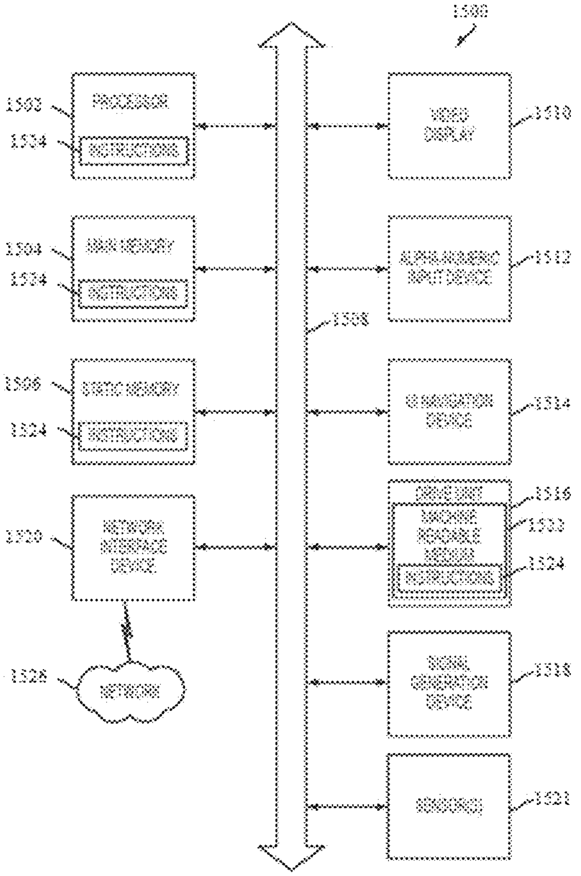
FIG. 15B is an exemplary block diagram illustrating an example of a machine upon which one or more aspects of embodiments of the present disclosure can be implemented.

FIG. 15B illustrates a block diagram of an example machine 1500 upon which one or more embodiments (e.g., discussed methodologies) can be implemented (e.g., run). Examples of machine 1500 can include logic, one or more components, circuits (e.g., modules), or mechanisms. Circuits are tangible entities configured to perform certain operations. In an example, circuits can be arranged (e.g., internally or with respect to external entities such as other circuits) in a specified manner. In an example, one or more computer systems (e.g., a standalone, client or server computer system) or one or more hardware processors (processors) can be configured by software (e.g., instructions, an application portion, or an application) as a circuit that operates to perform certain operations as described herein. In an example, the software can reside (1) on a non-transitory machine readable medium or (2) in a transmission signal. In an example, the software, when executed by the underlying hardware of the circuit, causes the circuit to perform the certain operations.

In an example, a circuit can be implemented mechanically or electronically. For example, a circuit can include dedicated circuitry or logic that is specifically configured to perform one or more techniques such as discussed, such as including a special-purpose processor, a field programmable gate array (FPGA) or an application-specific integrated circuit (ASIC). In an example, a circuit can comprise programmable logic (e.g., circuitry, as encompassed within a general-purpose processor or other programmable processor) that can be temporarily configured (e.g., by software) to perform the certain operations. It will be appreciated that the decision to implement a circuit mechanically (e.g., in dedicated and permanently configured circuitry), or in temporarily configured circuitry (e.g., configured by software) can be driven by cost and time considerations.

Accordingly, the term "circuit" is understood to encompass a tangible entity, be that an entity that is physically constructed, permanently configured (e.g., hardwired), or temporarily (e.g., transitorily) configured (e.g., programmed) to operate in a specified manner or to perform specified operations. In an example, given a plurality of temporarily configured circuits, each of the circuits need not be configured or instantiated at any one instance in time. For example, where the circuits include a general-purpose processor configured via software, the general-purpose processor can be configured as respective different circuits at different times. Software can accordingly configure a processor, for example, to constitute a particular circuit at one instance of time and to constitute a different circuit at a different instance of time.

In an exemplary embodiment circuits can provide information to, and receive information from, other circuits. In this example, the circuits can be regarded as being communicatively coupled to one or more other circuits. Where multiple of such circuits exist contemporaneously, communications can be achieved through signal transmission (e.g., over appropriate circuits and buses) that connect the circuits. In embodiments in which multiple circuits are configured or instantiated at different times, communications between such circuits can be achieved, for example, through the storage and retrieval of information in memory structures to which the multiple circuits have access. For example, one circuit can perform an operation and store the output of that operation in a memory device to which it is communicatively coupled. A further circuit can then, at a later time, access the memory device to retrieve and process the stored output. In an example, circuits can be configured to initiate or receive communications with input or output devices and can operate on a resource (e.g., a collection of information).

The various operations of method examples described herein can be performed, at least partially, by one or more processors that are temporarily configured (e.g., by software) or permanently configured to perform the relevant operations. Whether temporarily or permanently configured, such processors can constitute processor-implemented circuits that operate to perform one or more operations or functions. In an example, the circuits referred to herein can comprise processor-implemented circuits.

Similarly, the methods described herein can be at least partially processor-implemented. For example, at least some of the operations of a method can be performed by one or processors or processor-implemented circuits. The performance of certain of the operations can be distributed among the one or more processors, not only residing within a single machine, but deployed across a number of machines. In an example, the processor or processors can be located in a single location (e.g., within a home environment, an office environment or as a server farm), while in other examples the processors can be distributed across a number of locations.

The one or more processors can also operate to support performance of the relevant operations in a "cloud computing" environment or as a "software as a service" (SaaS). For example, at least some of the operations can be performed by a group of computers (as examples of machines including processors), with these operations being accessible via a network (e.g., the Internet) and via one or more appropriate interfaces (e.g., Application Program Interfaces (APIs).)

Example embodiments (e.g., apparatus, systems, or methods) can be implemented in digital electronic circuitry, in computer hardware, in firmware, in software, or in any combination thereof. Example embodiments can be implemented using a computer program product (e.g., a computer program, tangibly embodied in an information carrier or in a machine readable medium, for execution by, or to control the operation of, data processing apparatus such as a programmable processor, a computer, or multiple computers).

A computer program can be written in any form of programming language, including compiled or interpreted languages, and it can be deployed in any form, including as a stand-alone program or as a software module, subroutine, or other unit suitable for use in a computing environment. A computer program can be deployed to be executed on one computer or on multiple computers at one site or distributed across multiple sites and interconnected by a communication network.

In an example, operations can be performed by one or more programmable processors executing a computer program to perform functions by operating on input data and generating output. Examples of method operations can also be performed by, and example apparatus can be implemented as, special purpose logic circuitry (e.g., a field programmable gate array (FPGA) or an application-specific integrated circuit (ASIC)).

The computing system can include clients and servers. A client and server are generally remote from each other and generally interact through a communication network. The relationship of client and server arises by virtue of computer programs running on the respective computers and having a client-server relationship to each other. In embodiments deploying a programmable computing system, it will be appreciated that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware can be a design choice. Below are set out hardware (e.g., machine 1500) and software architectures that can be deployed in example embodiments.

In an example, the machine 1500 can operate as a standalone device or the machine 1500 can be connected (e.g., networked) to other machines. In a networked deployment, the machine 1500 can operate in the capacity of either a server or a client machine in server-client network environments. In an example, machine 1500 can act as a peer machine in peer-to-peer (or other distributed) network environments. The machine 1500 can be a personal computer (PC), a tablet PC, a set-top box (STB), a Personal Digital Assistant (PDA), a mobile telephone, a web appliance, a network router, switch or bridge, or any machine capable of executing instructions (sequential or otherwise) specifying actions to be taken (e.g., performed) by the machine 1500. Further, while only a single machine 1500 is illustrated, the term "machine" shall also be taken to include any collection of machines that individually or jointly execute a set (or multiple sets) of instructions to perform any one or more of the methodologies discussed herein.

Example machine (e.g., computer system) 1500 can include a processor 1502 (e.g., a central processing unit (CPU), a graphics processing unit (GPU) or both), a main memory 1504 and a static memory 1506, some or all of which can communicate with each other via a bus 1508. The machine 1500 can further include a display unit 1510, an alphanumeric input device 1512 (e.g., a keyboard), and a user interface (UI) navigation device 1511 (e.g., a mouse). In an example, the display unit 1510, input device 1512 and UI navigation device 1514 can be a touch screen display. The machine 400 can additionally include a storage device (e.g., drive unit) 1516, a signal generation device 1518 (e.g., a speaker), a network interface device 1520, and one or more sensors 1521, such as a global positioning system (GPS) sensor, compass, accelerometer, or other sensor.

The storage device 1516 can include a machine readable medium 1522 on which is stored one or more sets of data structures or instructions 1524 (e.g., software) embodying or utilized by any one or more of the methodologies or functions described herein. The instructions 1524 can also reside, completely or at least partially, within the main memory 1504, within static memory 1506, or within the processor 1502 during execution thereof by the machine 1500. In an example, one or any combination of the processor 1502, the main memory 1504, the static memory 1506, or the storage device 1516 can constitute machine readable media.

While the machine readable medium 1522 is illustrated as a single medium, the term "machine readable medium" can include a single medium or multiple media (e.g., a centralized or distributed database, and/or associated caches and servers) that configured to store the one or more instructions 1524. The term "machine readable medium" can also be taken to include any tangible medium that is capable of storing, encoding, or carrying instructions for execution by the machine and that cause the machine to perform any one or more of the methodologies of the present disclosure or that is capable of storing, encoding or carrying data structures utilized by or associated with such instructions. The term "machine readable medium" can accordingly be taken to include, but not be limited to, solid-state memories, and optical and magnetic media. Specific examples of machine readable media can include non-volatile memory, including, by way of example, semiconductor memory devices (e.g., Electrically Programmable Read-Only Memory (EPROM), Electrically Erasable Programmable Read-Only Memory (EEPROM)) and flash memory devices; magnetic disks such as internal hard disks and removable disks; magneto-optical disks; and CD-ROM and DVD-ROM disks.

The instructions 1524 can further be transmitted or received over a communications network 1526 using a transmission medium via the network interface device 1520 utilizing any one of a number of transfer protocols (e.g., frame relay, IP, TCP, UDP, HTTP, etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., IEEE 802.11 standards family known as Wi-Fi®, IEEE 802.16 standards family known as WiMax®), peer-to-peer (P2P) networks, among others. The term "transmission medium" shall be taken to include any intangible medium that is capable of storing, encoding or carrying instructions for execution by the machine, and includes digital or analog communications signals or other intangible medium to facilitate communication of such software.

Data Analysis

Figure 16:
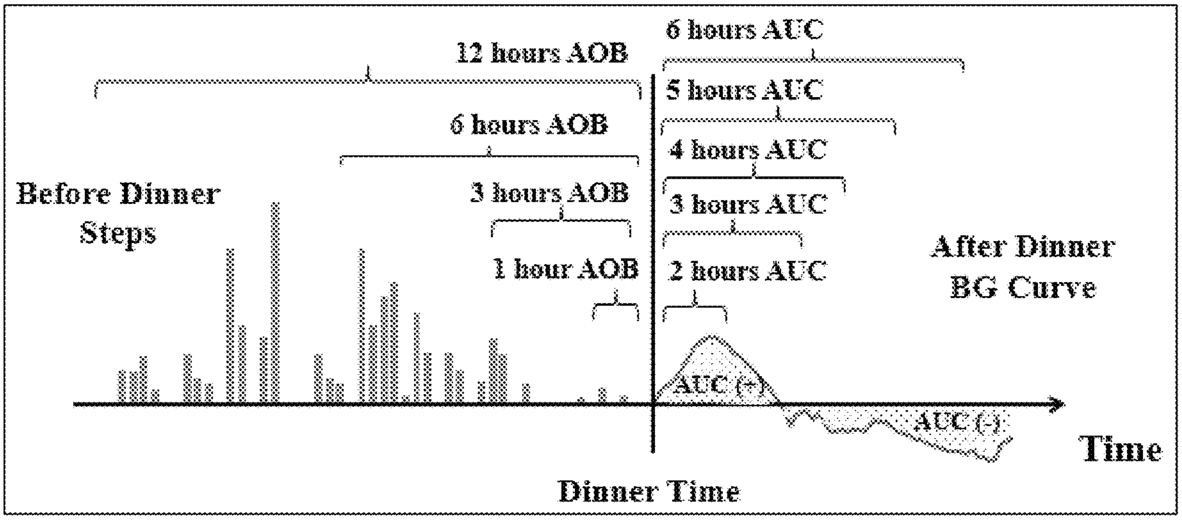
FIG. 16 is an exemplary representation of regression models that evaluated different preceding and following time spans before and after dinner time.

Data was obtained from 15 subjects with T1D with age range 21-65 years, HbA1c range 7-10% and currently using insulin pump therapy. Participants followed regular pump therapy for a month while wearing a blinded continuous glucose monitor and a physical activity tracker. Complete glucose, insulin, meal and activity datasets were obtained from 8 subjects (13.4±5.1 days/subject). Dinnertime meals were labeled and linear regression models were designed to assess impact of AOB for different retrospective time frames on BG excursion for 2 to 6 hours following dinner, as shown in FIG. 16. Dinner was chosen for the trial because (i) most of the daily PA has been performed by the time of dinner and (ii) the possibility of a big disturbance (e.g. meal, exercise) within the following hours was relatively lower.

The dependent variable is chosen as the area under post meal glucose excursion. It is quantified as the area under the postprandial CGM curve (GAUC) with respect to the CGM value at the meal time. This area is associated with the CGM value at the meal time, the amount of carbohydrates ingested and the amount of insulin in the blood stream. These variables form the core variables of the present regression models as follows: CGM value at the meal time ($CGM_{start}$), total carbohydrate on board ($COB_{start}$) that includes the meal itself and carbohydrates ingested within the 6 hour preceding the meal and total insulin on board at the meal time including the bolus associated with the selected meal ($IOB_{start}$). $COB_{start}$ can be calculated as the sum of previous meals with weighed exponentially based on their distance from the selected meal and $IOB_{start}$ involves deviations from patient's basal profile and boluses within the 4 hour preceding meal time.

Figure 17:
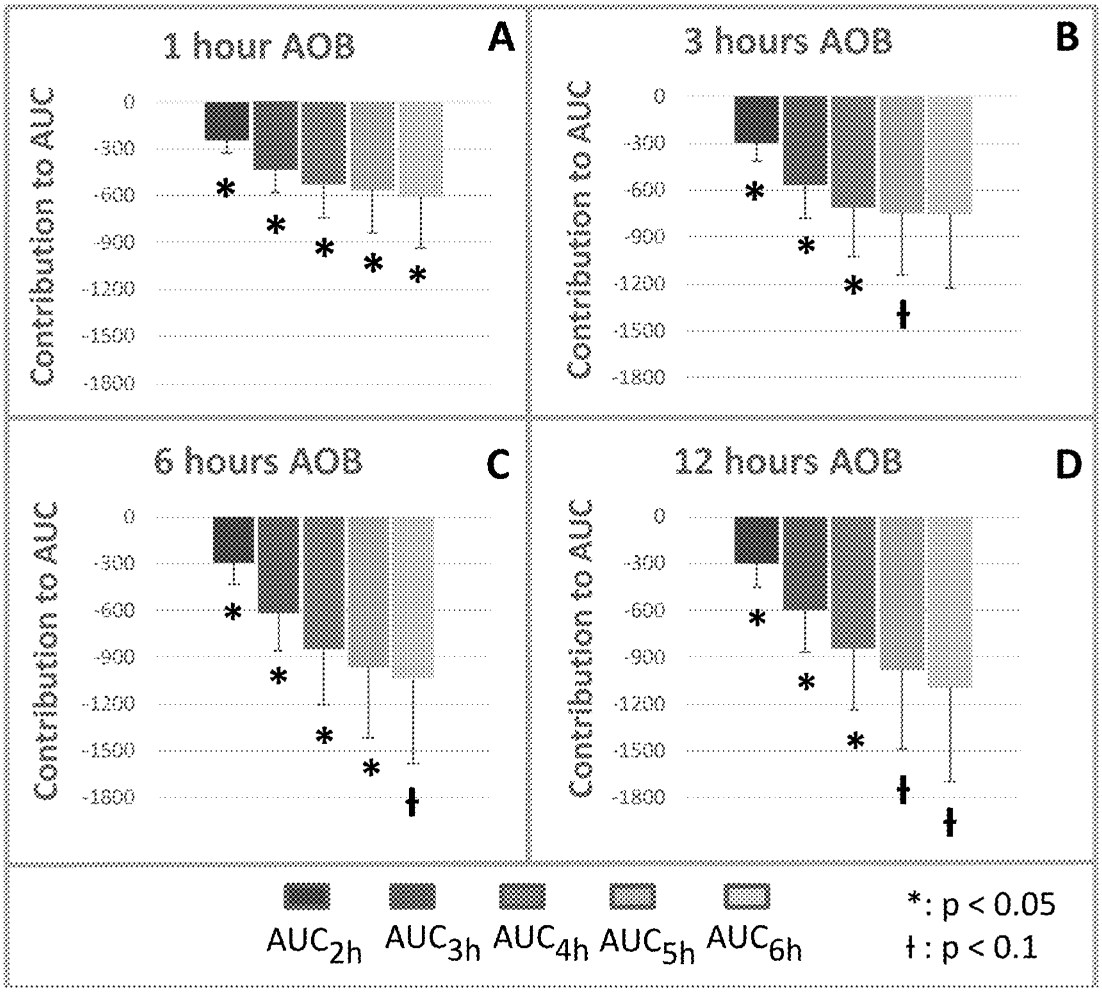
FIG. 17 shows exemplary contributions of AOB to glucose area under the postprandial curve (AUC)

The effect of 1-hour accumulated activity (panel A), as well as 3 h (panel B), 6 h (panel C) and 12 h (panel D) performed preceding the mealtime was studied. Impact on early vs late effect of activity was captured by observing AUC in the first 2, 3, 4, 5 and 6 hours post meal. The contribution of the AOB variable to AUC-calculated as the average value of the variable in the dataset multiplied by its regression coefficient—is represented by different bars in FIG. 17. Results showed that both early (2 hours) and late phases (4 to 5 hours) of postprandial glucose excursion were affected by antecedent PA ($p<0.1$). The recent PA had an impact on all time windows of postprandial phase (panel A) and the significant PA impact lasts up to 12 hours after the PA (panel D). This impact was in the direction of reducing the glucose area under the postprandial curve, hence the overall glucose exposure after dinner.

Data Analysis with an Augmented Dataset

The foregoing data analysis was augmented with data obtained from adults and adolescents with T1D in the age range 15-65 years, HbA1c range 7-10%. While the inpatient admissions were designed to test different treatment strategies, a standard outpatient data collection period of over 28 days were conducted leading to inpatient admissions in all of them. During the data collection periods, the participants followed their regular therapy for a month while wearing a CGM and a wristband PA tracker. Glucose measurements were collected through participants' own CGMs if they were already using one. Otherwise they were provided CGMs. All participants were provided with a PA tracker by the study team. Participants were instructed to download their personal insulin pump and CGM data and, synchronize their PA tracker at regular intervals. Another requirement of these studies were entering any consumed carbohydrates (meals, snacks and hypoglycemia treatment) via the bolus wizard of pumps for pump users and via an application for MDI users.

Data pre-processing: Outpatient data from 37 patients who completed the data collection periods successfully was obtained, and criteria on CGM, meal, bolus, PA data for a day to be considered valid were applied. Days with no bolused meal between 4:30 pm and 10 pm or with a total of more than 48 missing CGM data points between 4:30 pm and 10 pm were considered invalid for the analysis. When there is a CGM gap that does not violate these criteria, the missing value was replaced by interpolating the closest available CGM data. As for PA data validity, the existence of PA data in the morning (6 am to noon), afternoon (noon to 5 pm) and evening (5 pm to 10 pm) was checked separately. More than 2 hours of gap in any of these 3 sections would make the day invalid. Finally, first days of data collection period were included only if there is 12 hours of valid CGM, PA and pump data preceding the selected evening meal.

Regression Analysis on the Glycemic Impact of Previous PA—a dependent variable is chosen as the area under post meal glucose trace computed for 6 hours following the selected meals (GAUC-6 h). This area is associated with the CGM value at the meal time, the amount of carbohydrates ingested and the amount of insulin in the blood stream. These variables form the core variables of the present regression models as follows: CGM value at the meal time ($CGM_{start}$), total carbohydrate on board ($COB_{start}$) that includes the meal itself and carbohydrates ingested within the 6 hour preceding the meal and total insulin on board at the meal time including the bolus associated with the selected meal ($IOB_{start}$). $COB_{start}$ is calculated as the sum of previous meals with weighed exponentially based on their distance from the selected meal and $IOB_{start}$ involves deviations from patient's basal profile and boluses within the 4 hour preceding meal time.

Standardization across patients was achieved via dividing $COB_{start}$ by body weight and $IOB_{start}$ by patient's average total daily insulin and through linear mixed effect regression models where patient effect is included as a random effect.

Results—over the course of the data collection period, 1488 days of data was collected from 37 patients. Out of these days, 201 days were eliminated according to the CGM validity criterion; 120 days were eliminated for not having a bolused carbohydrate intake between 4:30 pm and 10 pm (101 days of no reported carbohydrate intake in the 4:30-10 pm, 6 days of no bolus, 13 days of no associated pairs of carbohydrate and insulin bolus). From the remaining dataset, 305 days got excluded according to the PA validity criteria explained in the data preprocessing section. When the total number of steps taken following the selected evening meal was higher than the total number of steps in the preceding 12 hours, the day is eliminated in order to isolate the impact of previous PA.

The final dataset consisted of 845 days with complete glucose, insulin, meal, and activity data obtained from 37 subjects (17 males, 20 females and 22.8±11.6 days/subject) with age range 17-62 years (41.1±12.2), HbA1c range 5.3-9.2% (7.1±0.9). Eight of these patients were on multiple daily injections while the rest were pump users. Average values of the covariates in this final dataset was 152.4±60.6 mg/dl for $CGM_{start}$, 0.15±0.07 for $IOB_{start}$/TDI, 0.7±0.3 gr/kg for $COB_{start}$/BW. This final dataset is used in the regression models.

Regression results in Table 1 below demonstrate that the total number of steps taken within 12 hours preceding mealtime has statistically significant association with the GAUC-6 h following the meal.

TABLE 1

Regression results: Association of GAUC-6 h with total steps taken within the preceding 12 hours.

| | Coefficient | p-value |
|---|---|---|
| Intercept | 72.3 ± 231.9 | 0.76 |
| CGMstart | −46.8 ± 1.9 | <0.01* |
| COBstart/BW | 1248.4 ± 408.5 | <0.01* |
| IOBstart/TDI | −7621.4 ± 2003.1 | <0.01* |
| Ln(Total Steps) | −458.2 ± 223.4 | 0.04* |

Figure 18:
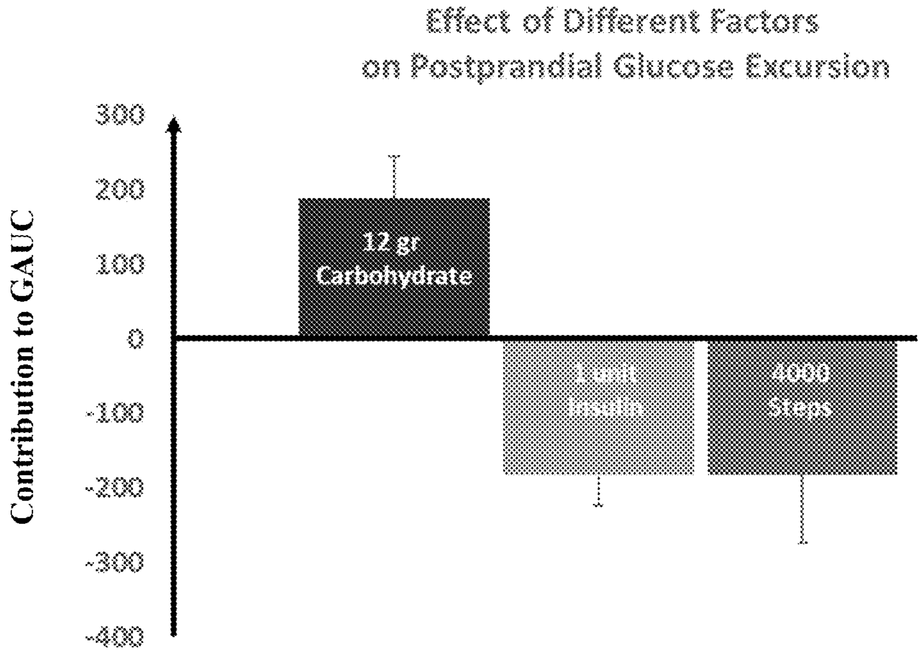
FIG. 18 shows an exemplary effect of different factors on postprandial glucose excursion.

Results in Table 1 can be translated into clinical use by mapping the increment in the accumulated PA with an amount of insulin that has an equivalent glycemic impact on post-meal GAUC. FIG. 18 provides an example based on the average values for the independent variables in the present dataset.

Regression Analysis on the Glycemic Impact of Previous PA—to assess the effect of PA performed during each hour within the 12 hour time frame prior to the selected meals, individual linear mixed effects models were designed. Each model had core independent variables and a PA variable computed as the total number of steps taken in a separate hour within the explored period. The response variable was kept the same as GAUC-6 h.

Results from 12 separate regression analyses support the results of a previous study incorporated here by reference (McMahon S K, Ferreira L D, Ratnam N, Davey R J, Youngs L M, Davis E A, et al. Glucose Requirements to Maintain Euglycemia after Moderate-Intensity Afternoon Exercise in Adolescents with Type 1 Diabetes Are Increased in a Biphasic Manner. J Clin Endocrinol Metab. 2007 Mar. 1; 92(3): 963-8), where a biphasic PA impact was observed. The pattern of regression coefficients of hourly PA variables are in favor of a late-onset second high glycemic impact (from 6th hour until 10th hours) of PA separate from its immediate impact. This second impact appears after a silent period similar to what McMahon et al. observed in their inpatient glucose clamp study.

Figure 19:
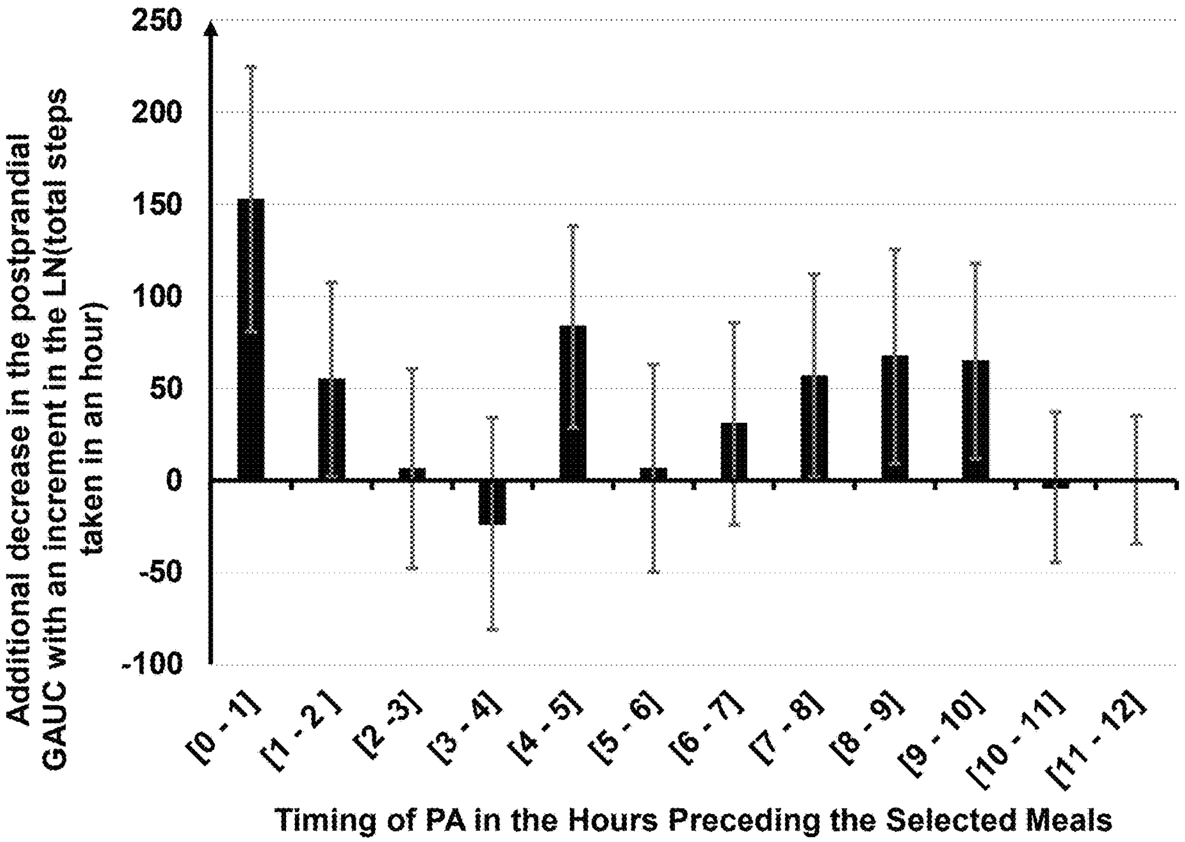
FIG. 19 shows a bar plot representation of the observed magnitude of decrease in the postprandial GAUC with an increment in the LN (total number of steps taken) for each hour preceding the mealtime (e.g. [0-1]: the hour right before the meal)

FIG. 19 shows a bar plot representation of the observed magnitude of decrease in the postprandial GAUC with an increment in the LN (total number of steps taken) for each hour preceding the mealtime (e.g. [0-1]: the hour right before the meal). These results are obtained from 12 separate LME models. These results and the results obtained in the referenced study (McMahon S K, Ferreira L D, Ratnam N, Davey R J, Youngs L M, Davis E A, et al. Glucose Requirements to Maintain Euglycemia after Moderate-Intensity Afternoon Exercise in Adolescents with Type 1 Diabetes Are Increased in a Biphasic Manner. J Clin Endocrinol Metab. 2007 Mar. 1; 92(3):963-8) suggest a late-onset second glycemic impact of PA separate from its immediate impact. Such a biphasic impact would be particularly important in insulin dosing adjustments regarding PA. While most of the PA related glucose control suggestions are towards decreasing the insulin doses in the hours following PA, this may result in hyperglycemia when done during a silent period where PA does not have an observed impact on glucose uptake. This suggests a need to understand the specifics of the PA-glucose behavior dynamics for proper treatment adjustments regarding PA in T1D.

These analyses, therefore, show that (i) daily accumulated activity can be quantified by a ubiquitously available activity indicator; step count and (ii) daily accumulated PA had a statistically significant impact on post dinner glycemic exposure.

Post dinner glycemic excursions in simulation with the data collected from 29 insulin pump users (13 males and 16 females, 20.6±11.1 day/patient) was assessed. Average AOB at 5 pm was 2949±1303. The experiment replayed-in-silico-the recorded insulin boluses starting from the dinner meal until 11 pm for every patient's all available days and compared the performances of the following treatment policies—1) standard insulin therapy with patients' original treatment parameters (represented as "FIT"), which is considered as the baseline treatment; 2) the present method (represented as "AF*"); and 3) standard insulin therapy with optimized CR (optimum CR without PA information) to understand the performance of FIT with optimum CR and without any PA information.

Figure 20:
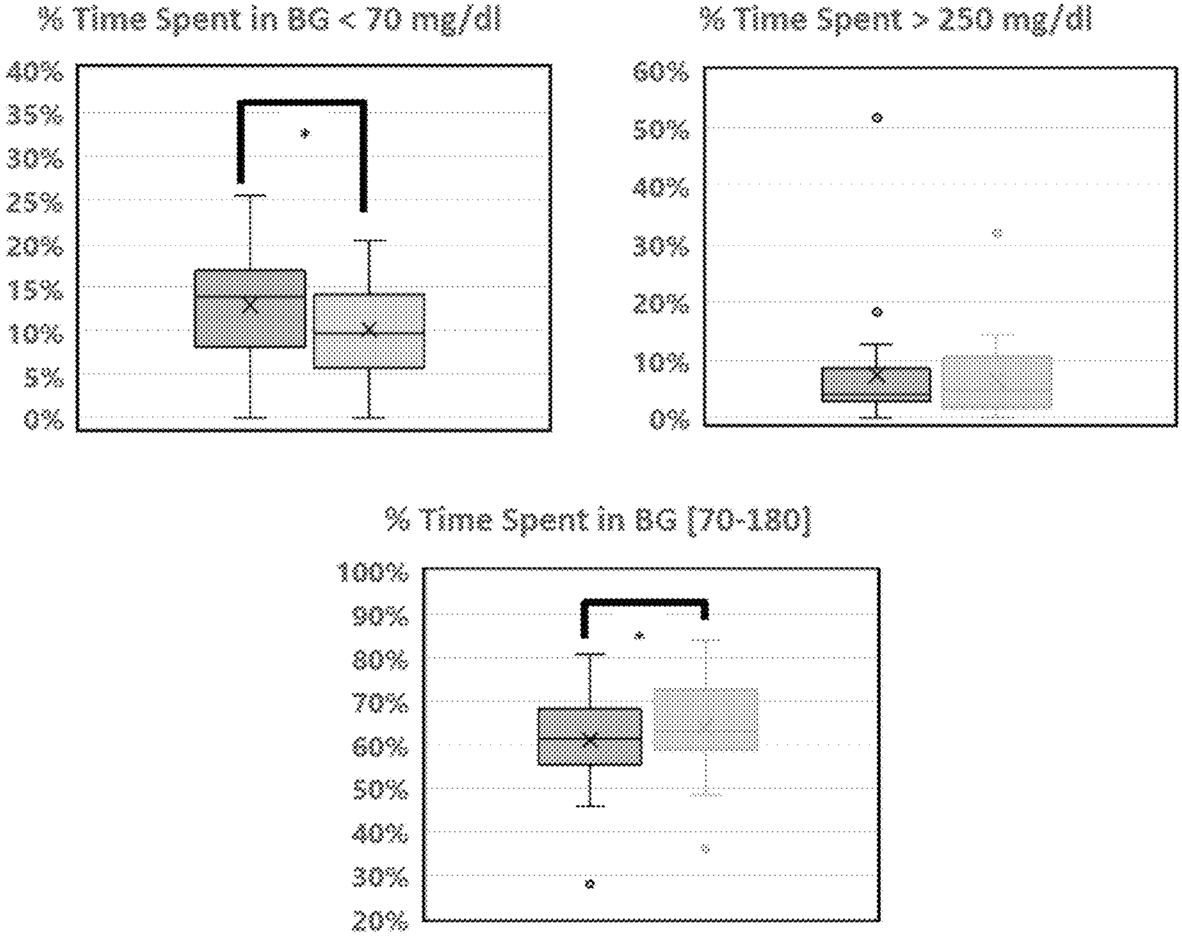
FIG. 20 illustrates exemplary in-silico application results of a comparison of time spent in different BG levels for FIT vs PA informed bolus method.

FIG. 20 illustrates that the present method can yield a lower percentage of time in hypoglycemia (FIT: % 13.1±7.5, AF*: % 9.5±5, p=0.001) and a higher percentage of time in euglycemic range (FIT: % 64±11.3, AF*: % 65±11.4, p=0.006) with no significant difference in the time spent in CGM>250 mg/dl (FIT: % 7.6±0.01, AF*: % 7±0.005, p=0.43). The disclosed optimization to find AF pairs that would benefit the glycemic control failed to find any value for 9 patients out of 29 (no AF1 found for 6 patients, no AF2 was found for 7 patients with an intersection of 4 patients). Additionally, 3 patients had one of their AFs>20,000 (average for AF1 6825±3229 and AF2 5683±2159 in the present dataset).

Figure 21:
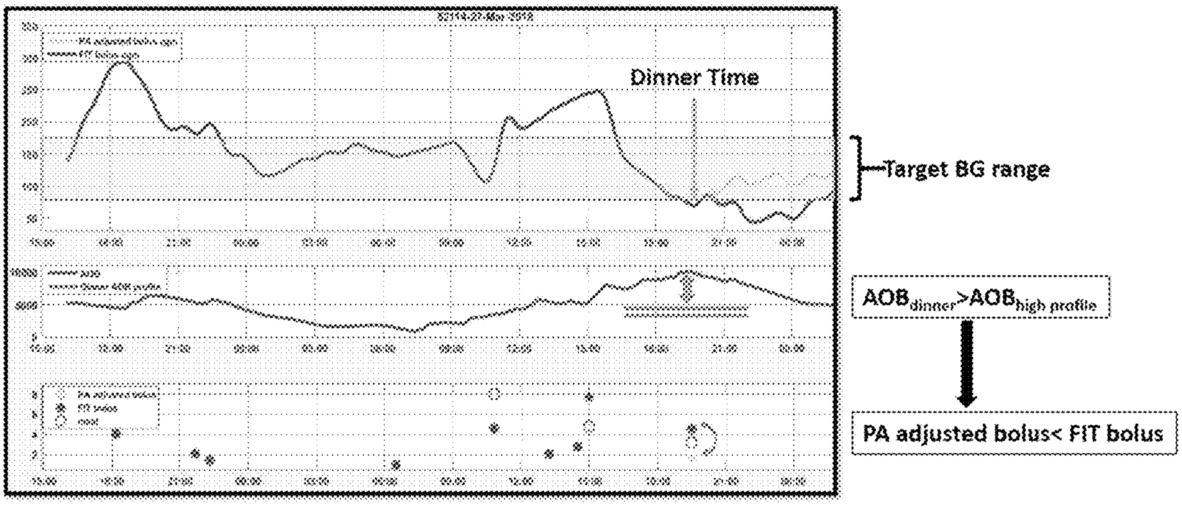
FIG. 21 illustrates an exemplary in silico sample application of PA informed insulin bolus adjustment.

FIG. 21 illustrates an exemplary in silico sample application of PA informed insulin bolus adjustment. The next few paragraphs describe a testing safety and feasibility of activity informed treatment method in daily life to demonstrate safety and feasibility of a decision support system for activity-related insulin boluses in T1D. Since in daily life, patients with Type 1 diabetes often need to adjust insulin boluses to account for activity, the disclosed method can make better bolus decisions by integrating knowledge about daily PA into bolus decisions-computationally-. It can decrease risk of hypoglycemia related to previous PA and provide better overall glucose control.

The disclosed procedures have useful applications outside of the diabetes context. For example, automobile driver assistance systems have analogous functions to BG control systems in the following respects, for which the disclosed methodology can be put to use in this new context, described as follows.

Data collection that represents the impulse responses for whole state space is challenging due to variety of road conditions, changes in the car human behavior, different features of the cars, etc. PA in T1D causes a prolonged difference in the glucose response to meals and insulin. Weather conditions would cause a difference in the speed response to the same braking and speeding actions For any kind of driver assistance strategy, human behavior and unexpected disturbances are factors that need to be taken into account. It is also a safety critical system. Optimum control parameters are different from driver to driver (as it is from patient to patient). These optimum control parameters for the average conditions would not be optimum in case of a significant disturbance and would need to be corrected.

Bumps on the road, weather changes, unexpected break by the front car and many disturbances that are difficult to model may occur at any point in time. It is easier to take action for one disturbance at a time especially if the impulse response is known. However, in daily life, people eat, inject insulin and exercise different amounts in different orders and frequencies. The performance of any advisory system will be impacted by difference in this kind of behaviors and the system must be safe for these unexpected occurrences.

Changes in the gas features, temperature, vehicle maintenance condition may yield different responses to same inputs and/or disturbances. Glucose response to the same inputs (i.e. meal, insulin, PA) can differ for different metabolic states, health vs sickness, psychological stress and idiosyncratic factors.

According to National Center for Statistics and Analysis, 29.7% of all crashes in 2000 were rear-end crashes. Car collisions can be thought similar to the hypoglycemic events in T1D. They both can mostly be prevented by the user/patient through frequent monitoring of the system and taking the correct action. However, in both cases, the correct action that would yield the "optimum outcome" is not always clear due to the lack of quantifiable measures for the system disturbances and difficulty of being able to keep frequent monitoring, making the correct decision on different occasions. The analogy can be made as follows.

Automatic brake assistance in advanced cruise control could take action for a bump on the road or rainy weather to prevent a rear-end collision. Mild and moderate PA in T1D are disturbances to the system that require reduction of insulin to prevent a hypoglycemic event. The disclosed insulin adjustment system takes action to prevent PA-related hypoglycemia in T1D.

An auto brake system which addresses rear-end collisions at low speeds is designed to avoid collisions on the urban roads where the car's speed is below around 30 km/h. Low speeds can be thought analogous to unstructured daily PA. Both the auto brake system and the disclosed system consist of a sensor and a controller. In the auto brake system, sensor measures the distance from the targets that create potential for a collision; the controller assesses these threats and activates the automatic brake system when necessary in different real life city driving scenarios. These steps are very similar to hypoglycemia prediction and prevention in T1D.

While these systems would work well in standard conditions, it can be important to adjust the control actions in certain cases. For example, the time and power it takes for the vehicle to stop would be different under rainy weather or different road conditions (e.g. different surface texture). Similarly, in case of PA, the action required to prevent hypoglycemia is different than the one required in no PA case. The methodology provided for integrating PA into insulin bolus decisions may be applied for the adjustment of the parameters of an automatic brake system for different conditions. Furthermore, any system that has similar challenges could benefit from an extension of the perspective, ideas and methods that will be obtained during this research effort.

It should be appreciated that the system, method, device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required. It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It should also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing examplary embodiments, terminology has been used for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the nth reference in the list. All references cited and discussed in this specification are incorporated herein by reference in their entireties and to the same extent as if each reference was individually incorporated by reference.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5).

Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

It should be appreciated that any of the components or modules referred to with regards to any of the present embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

It will be appreciated by those skilled in the art that the present disclosure can be embodied in other specific forms without departing from the spirit or essential characteristics thereof. The presently disclosed embodiments are therefore considered in all respects to be illustrative and not restricted. The scope of the disclosure is indicated by the appended claims rather than the foregoing description and all changes that come within the meaning and range and equivalence thereof are intended to be embraced therein.

What is claimed is:

1. A method of adjusting insulin bolus for optimized control of a computer-implemented functional insulin treatment therapy by maintaining a low blood glucose (BG) variability, the method comprising:

quantifying physical activity (PA) of a patient;

calculating an accumulated PA based on the quantified PA, the accumulated PA indicating an aggregate of the PA that has an impact on blood glucose (BG) uptake for the patient;

generating a previous activity component based on an account of the accumulated PA over time period (t), the previous activity component including a band defined by a range of accumulated PA levels in which no PA-related insulin adjustment occurred during time period t;

at a time of a bolus decision:

adjusting a prevalent functional insulin therapy bolus using the previous activity component to generate an activity informed insulin bolus when accumulated PA for an activity component over time period (T) is outside the band of accumulated PA levels; and generating a signal to cause an insulin delivery device to administer the activity informed insulin bolus to the patient;

wherein:

time period t includes a time that precedes a time in time period T; and a timespan for time period t corresponds to a timespan for time period T.

2. The method of claim 1, comprising:

calculating the prevalent functional insulin therapy bolus based on a meal component, a correction component, and a previous insulin component, wherein the correction component indicates an amount of insulin required to compensate for a difference between a target BG level and current BG level.

3. The method of claim 2, comprising:

calculating the meal component based on a ratio of an estimated carbohydrate intake and an amount of carbohydrate compensated by one unit of insulin.

4. The method of claim 2, comprising:

calculating the correction component based on current blood glucose (BG), target BG, and a correction factor that indicates a decrease in BG resulting from a single unit of the insulin.

5. The method of claim 2, comprising:

determining the previous insulin component based on insulin that is in circulation due to previous insulin injections.

6. The method of claim 1, wherein the previous activity component is also based on an activity profile, the method comprising:

determining the activity profile by calculating a median of the accumulated PA measured at a specific time of a day for multiple days.

7. The method of claim 1, wherein the previous activity component is also based on an activity factor, the method comprising:

determining the activity factor by calculating an amount of the accumulated PA that has a same impact on BG of the patient as a single unit of insulin.

8. The method of claim 1, wherein the quantifying of PA comprises:

measuring a step count of the patient.

9. The method of claim 1, wherein the accumulated PA is calculated using a weighted sum of the quantified PA over a period of time.

10. The method of claim 1, wherein the calculating of the accumulated PA occurs at a time of bolus calculation for the patient.

11. The method of claim 1, comprising:

administering the activity informed insulin bolus to the patient.

12. The method of claim 1, wherein:

adjusting the prevalent functional insulin therapy bolus by a first adjustment when accumulated PA for the activity component over time period T is above the band of accumulated PA levels; and adjusting the prevalent functional insulin therapy bolus by a second adjustment when accumulated PA for the activity component over time period T is below the band of accumulated PA levels;

wherein the first adjustment and/or the second adjustment is based on an objective function.

13. A dosing device, comprising:

a processor having associated memory with instructions stored thereon that, when executed, causes the processor to adjust insulin bolus for optimized control of a functional insulin treatment therapy by maintaining a low blood glucose (BG) variability, the instructions causing the processor to:

quantify physical activity (PA) of a patient;

calculate an accumulated PA based on the quantified PA, the accumulated PA indicating an aggregate of the PA that has an impact on blood glucose (BG) uptake for the patient;

generate a previous activity component based on an account of the accumulated PA over time period (t), the previous activity component including a band defined by a range of accumulated PA levels in which no PA-related insulin adjustment occurred during time period t;

at a time of a bolus decision:

adjust a prevalent functional insulin therapy bolus using the previous activity component to generate an activity informed insulin bolus when accumulated PA for an activity component over time period (T) is outside the band of accumulated PA levels; and generate a signal to cause the processor or another processor to administer the activity informed insulin bolus to the patient;

wherein:

time period t includes a time that precedes a time in time period T; and a timespan for time period t corresponds to a timespan for time period T.

14. The dosing device of claim 13, wherein instructions cause the processor to:

adjust the prevalent functional insulin therapy bolus by a first adjustment when accumulated PA for the activity component over time period T is above the band of accumulated PA levels; and adjust the prevalent functional insulin therapy bolus by a second adjustment when accumulated PA for the activity component over time period T is below the band of accumulated PA levels;

wherein the first adjustment and/or the second adjustment is based on an objective function.

15. A system for adjusting insulin bolus for optimized control of a functional insulin treatment therapy by maintaining a low blood glucose (BG) variability, the system comprising:

a dosing device configured to administer insulin;

a quantifying module including a processor configured to quantify physical activity (PA) of a patient;

an accumulation module including a processor configured to:

calculate an accumulated PA based on the quantified PA, the accumulated PA indicating an aggregate of the PA that has an impact on blood glucose (BG) uptake for the patient; and generate a previous activity component based on an account of the accumulated PA over time period (t), the previous activity component including a band defined by a range of accumulated PA levels in which no PA-related insulin adjustment occurred during time period t;

a generation module including a processor configured to:

at a time of a bolus decision:

adjust a prevalent functional insulin therapy bolus using the previous activity component to generate an activity informed insulin bolus when accumulated PA for an activity component over time period (T) is outside the band of accumulated PA levels, wherein time period t includes a time that precedes a time in time period T, and a timespan for time period t corresponds to a timespan for time period T; and generate a signal to cause the dosing device to administer the activity informed insulin bolus to the patient.

16. The system of claim 15, wherein the prevalent functional insulin therapy bolus is based on a meal component, a correction component, and a previous insulin component, wherein the correction component indicates an amount of insulin required to compensate for a difference between a target BG level and current BG level.

17. The system of claim 16, wherein the meal component is based on a ratio of an estimated carbohydrate intake and an amount of carbohydrate compensated by one unit of insulin.

18. The system of claim 16, wherein the correction component is based on current BG, target BG, and a correction factor that indicates a decrease in BG resulting from a single unit of the insulin.

19. The system of claim 16, wherein the previous insulin component is based on insulin that is in circulation due to previous insulin injections.

20. The system of claim 15, wherein the previous activity component is also based on an activity profile, and the activity profile is based on a median of the accumulated PA measured at a specific time of a day for multiple days.

21. The system of claim 15, wherein the previous activity component is also based on an activity factor, and the activity factor is based on an amount of the accumulated PA that has a same impact on BG of the patient as a single unit of insulin.

22. The system of claim 15, comprising:

a pedometer to measure a step count to quantify the PA of the patient.

23. The system of claim 15, wherein the accumulated PA is calculated using a weighted sum of the quantified PA over a period of time.

24. The system of claim 15 implemented in an open or closed loop blood glucose control algorithm.

25. The system of claim 15, wherein the generation module:

adjusts the prevalent functional insulin therapy bolus by a first adjustment when accumulated PA for the activity component over time period T is above the band of accumulated PA levels; and adjusts the prevalent functional insulin therapy bolus by a second adjustment when accumulated PA for the activity component over time period T is below the band of accumulated PA levels;

wherein the first adjustment and/or the second adjustment is based on an objective function.

* * * * *